US005214191A

United States Patent [19]

Kirschenheuter et al.

[11] Patent Number: 5,214,191

[45] Date of Patent: May 25, 1993

[54] OXIDANT SENSITIVE AND INSENSITIVE AROMATIC ESTERS AS INHIBITORS OF HUMAN NEUTROPHIL ELASTASE

[75] Inventors: Gary P. Kirschenheuter; Lyle W. Spruce, both of Arvada; John C. Cheronis, Lakewood, all of Colo.

[73] Assignee: Cortech, Inc., Denver, Colo.

[21] Appl. No.: 528,967

[22] Filed: May 22, 1990

[51] Int. Cl.[5] .............. C07C 69/76

[52] U.S. Cl. .............. 514/231.8; 560/9; 560/11; 560/19; 560/45; 560/56; 560/59; 560/100; 560/102; 560/106; 560/105; 548/343.5; 548/475; 548/545; 548/313.7; 544/171; 544/392; 549/350; 549/362; 514/315; 514/399; 514/425; 514/450; 514/452; 514/456; 514/532; 514/239.5

[58] Field of Search .............. 560/105, 9, 11, 19, 560/45, 56, 59, 100, 102, 106; 548/341, 475, 545; 544/171, 392; 549/350, 362; 514/240, 315, 399, 425, 450, 452, 456, 532

[56] References Cited

U.S. PATENT DOCUMENTS

| | | | |
|---|---|---|---|
| 3,954,767 | 5/1976 | Esteve-Subirana | 260/268 R |
| 4,115,648 | 9/1978 | Esteve-Subirana | 544/110 |
| 4,567,288 | 1/1986 | Cousse et al. | 560/37 |
| 4,698,344 | 10/1987 | Sasse et al. | 514/275 |

FOREIGN PATENT DOCUMENTS

| | | |
|---|---|---|
| 0068998 | 1/1983 | European Pat. Off. . |
| 0183159 | 6/1986 | European Pat. Off. . |
| 2459614 | 11/1975 | Fed. Rep. of Germany . |

OTHER PUBLICATIONS

CA 109 (7):54438m 1988.
CA 114 (10):88647x 1990.
CA 105 (17):153057k 1986.

*Primary Examiner*—Paul J. Killos
*Attorney, Agent, or Firm*—Cushman, Darby & Cushman

[57] ABSTRACT

2-Phenylalkanoate esters which are useful as inhibitors of human leukocyte elastase.

15 Claims, No Drawings

OXIDANT SENSITIVE AND INSENSITIVE AROMATIC ESTERS AS INHIBITORS OF HUMAN NEUTROPHIL ELASTASE

The present invention relates to certain 2-phenylalkanoate esters which are useful as inhibitors of human leukocyte elastase (HLE) or equivalently human neutrophil elastase (HNE).

BACKGROUND OF THE INVENTION

There has been considerable research effort in recent years toward the development of HLE inhibitors because it appears that HLE may be responsible for a variety of human diseases. For example, tests have shown that there is an apparent association between HLE and emphysema in Sandberg et al., *The New England Journal of Medicine,* 304:566 (1981). Other diseases and medical problems, such as arthritis and related inflammatory conditions and dermatitis, have also been associated with HLE. Accordingly, there is a need for compounds which are effective to inhibit HLE.

Typical prior efforts to deal with elastase inhibition are disclosed in the patent literature, for instance, U.S. Pat. Nos. 4,683,241 and 4,801,610.

SUMMARY OF THE INVENTION

The principal object of the present invention is to provide certain new compounds which are useful as elastase inhibitors. These compounds are characterized by their relatively low molecular weight and high selectivity with respect to HLE. As a consequence, they can be used to prevent, alleviate or otherwise treat disease characterized by the degradation effects caused by HLE on connective tissues in mammals, including humans.

The compounds of the invention may be structurally illustrated by the following formula (VI):

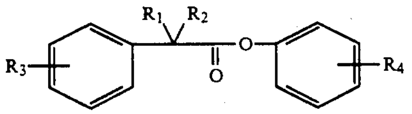

(VI)

wherein:

$R_1$ and $R_2$, which may be the same or different, are selected from the group consisting of:

- hydrogen, alkyl of 1-6 carbons, cycloalkyl of 3 to 6 carbons or together represent a methylene group $-(CH_2)_n-$ where n is a whole number of from 1 to 6;

$R_3$ represents one or more substituents up to five selected from the group consisting of:

- hydrogen, halogen, haloalkyl of 1-12 carbons (e.g. $CF_3$), alkyl of 1-12 carbons, alkoxy of 1-12 carbons, cycloalkyl of 3-12 carbons, alkenyl of 2 to 12 carbons, mono- or dicyclic aryl (e.g. optionally substituted phenyl or naphthyl),
- $-ZR_5$ where Z is O, S, S(O) or $SO_2$ and $R_5$ is hydrogen alkyl of 1-18 carbons, cycloalkyl of 3-12 carbons or phenyl;
- $-NR_6R_7$ where $R_6$ and $R_7$ may be the same or different and may be hydrogen, alkyl of 1-12 carbons, cycloalkyl of 3-6 carbons, phenyl, alkoxy of 1-12 carbons, acyl of the formula $-C(O)R_8$ where $R_8$ is alkyl of 1-12 carbons, cycloalkyl of 3-12 carbons, phenyl, $CH_3OC(O)CH_2CH_2-$, $HOOCCH_2CH_2-$, $NaO_3SCH_2CH_2NHC(O)CH_2CH_2-$, or $R_6$ and $R_7$ together represent $-C(O)CH_2CH_2C(O)-$, $-C(O)-C_6H_4-C(O)-$ or $-(CH)_2)_x-$ where x is 2, 3, 4, 5 or 6;
- morpholino, imidazole or piperazino joined to the phenyl ring through a nitrogen atom; or $R_3$ represents the atoms necessary to complete between adjacent ring carbons a further carbocyclic ring of from 1 to 6 carbons or a 5-6 membered heterocyclic ring including one or more O, S or N ring atoms; and

- $R_4$ is from one to five substituents selected from hydrogen, halogen, nitro, $-C(O)CH_3$, $S(O)_pR_9$ where p is 0, 1 or 2 and $R_9$ is hydroxy, —ONa or optionally substituted alkyl of 1-12 carbons or optionally substituted cycloalkyl including, for example, lower alkyl substituted with halogen (such as trifluoromethyl) or lower alkyl bearing a carboxylic acid group, especially $-CH_2C(CH_3)_2CO_2H$.

According to the invention, the phenyl rings may be unsubstituted (i.e. $R_3$ and $R_4$ may both be hydrogen). However, it is preferred that at least $R_4$ be other than hydrogen.

It will be appreciated that when $R_1$ and $R_2$ are different, the carbon atom to which these substituents are attached (i.e. the "alpha carbon") is a chiral center and the resulting compounds may exist in enantiomerically pure form or as racemic mixtures of the enantiomers. The invention contemplates such mixtures (+/−) as well as the separate (+ or −) enantiomers thereof.

Non-toxic pharmaceutically acceptable salts of the indicated compounds are also contemplated.

PREFERRED EMBODIMENTS OF THE INVENTION

Particularly advantageous for present purposes are the compounds of formula (VI) where one of $R_1$ and $R_2$ is hydrogen and the other is alkyl, particularly ethyl; and $R_3$ is hydrogen, lower alkyl, cycloalkyl, lower alkoxy, phenyl, the atoms necessary to complete an optionally substituted ring with the adjacent phenyl group, piperidino or $-NR_6R_7$ where $R_6$ is hydrogen and $R_7$ is $-C(O)R_8$ where $R_8$ is phenyl or where $R_6$ and $R_7$ together represent $-(CH_2)_x-$ where x is 2-6. The optional substitution in the case of $R_3$ may be, for example, lower alkyl or lower alkoxy, it being understood that reference herein to lower alkyl or lower alkoxy contemplates up to 6 carbon atoms.

As a further feature of the invention, it has been found that compounds which have been modified so as to remove the chiral center at the alpha carbon, i.e. by making $R_1$ and $R_2$ the same, e.g. either methyl or ethyl, or by merging $R_1$ and $R_2$ into a cycloalkyl ring (such as cyclopropyl, cyclobutyl, cyclopentyl or cyclohexyl) are particularly advantageous for use as human neutrophil elastase inhibitors.

According to a further aspect of the invention, it has been found that compounds wherein $R_4$ is $-SCH_3$ in the ortho or para positions, or where $R_4$ is $-S-CH_2C(CH_3)_2COOH$ in the para position, are particularly useful. These compounds appear to be oxidatively activatable as in vivo inhibitors, i.e. the —S— (sulfide) group seems to be oxidized in situ to the sulfoxide —S(O)— or to the sulfone $-S(O)_2-$. In this regard, it has been found that the potency of the compounds where $R_4$ is —S— (sulfide), —S(O)— (sulfoxide) and $-S(O)_2-$ (sulfone) increases in the series as follows:

$$-S- < -S(O)- < -S(O)_2-$$

Consequently, it appears that the potency of the —S— compounds can be increased by oxidants present at the site of HLE mediated damage to form the corresponding sulfoxides or sulfones.

Representative compounds according to the invention are shown in the following Tables I and II.

TABLE I

This table exemplifies compounds of the formula (VI) wherein $R_1$–$R_4$ have the values indicated. Positioning of the substituents represented by $R_3$ and/or $R_4$ is specified numerically, the link of the ring to the rest of the molecule being the 1-postion. Where two or more substituents are involved, each position is identified.

| Compound No. | $R_1$ | $R_2$ | $R_3$ | $R_4$ |
|---|---|---|---|---|
| 1) | H | $C_2H_5$ | H | 4-$SCH_3$ |
| 2) | H | $C_2H_5$ | H | 4-$\overset{\overset{O}{\|}}{S}CH_3$ |
| 3) | H | $C_2H_5$ | H | 4-$\overset{\overset{O}{\|}}{\underset{\underset{O}{\|}}{S}}CH_3$ |
| 4) | H | $C_2H_5$ | H | 4-$NO_2$ |
| 5) | H | $C_2H_5$ | H | 2-$SCH_3$ |
| 6) | H | $C_2H_5$ | H | 2-$\overset{\overset{O}{\|}}{S}CH_3$ |
| 7) | H | $C_2H_5$ | H | 2-$\overset{\overset{O}{\|}}{\underset{\underset{O}{\|}}{S}}CH_3$ |
| 8) | H | $C_2H_5$ | H | 3-F, 4-$NO_2$ |
| 9) | H | $C_2H_5$ | H | 4-$NO_2$ |
| 10) | H | $C_2H_5$ | H | 2,4-$NO_2$ |
| 11) | H | $C_2H_5$ | H | 2-$NO_2$ |
| 12) | H | $C_2H_5$ | H | 3-$NO_2$ |
| 13) | H | $C_2H_5$ | H | 4-F |
| 14) | H | $C_2H_5$ | H | 2,3,4-F |
| 15) | H | $C_2H_5$ | H | 3,4,5-F |
| 16) | H | $C_2H_5$ | H | 2,6-F |
| 17) | H | $C_2H_5$ | H | 2,3,5,6-F |
| 18) | H | $C_2H_5$ | H | 4-$SO_3Na$ |
| 19) | H | $C_2H_5$ | H | 3-$\overset{\overset{O}{\|}}{C}CH_3$ |
| 20) | H | $C_2H_5$ | H | 4-$\overset{\overset{O}{\|}}{C}CH_3$ |
| 21) | H | $C_2H_5$ | 4-$OCH_3$ | 3-$CH_3$, 4-$SCH_3$ |
| 22) | H | $C_2H_5$ | 4-$OCH_3$ | 3-$CH_3$, 4-$\overset{\overset{O}{\|}}{S}CH_3$ |
| 23) | H | $C_2H_5$ | 4-$OCH_3$ | 3-$CH_3$, 4-$\overset{\overset{O}{\|}}{\underset{\underset{O}{\|}}{S}}CH_3$ |
| 24) | H | $C_2H_5$ | 4-$OCH_3$ | 3-$CH_3$, 4-$NO_2$ |
| 25) | H | $C_2H_5$ | 4-$OCH_3$ | 2-$CH_3$, 4-$SCH_3$ |
| 26) | H | $C_2H_5$ | 4-$OCH_3$ | 2-$CH_3$, 4-$\overset{\overset{O}{\|}}{S}CH_3$ |
| 27) | H | $C_2H_5$ | 4-$OCH_3$ | 2-$CH_3$, 4-$\overset{\overset{O}{\|}}{\underset{\underset{O}{\|}}{S}}CH_3$ |
| 28) | H | $C_2H_5$ | 4-$OCH_3$ | 2$CH_3$, 4-$NO_2$ |
| 29) | H | $C_2H_5$ | 4-$OCH_3$ | 2,6-$CH_3$, 4-$SCH_3$ |

TABLE I-continued

This table exemplifies compounds of the formula (VI) wherein $R_1$-$R_4$ have the values indicated. Positioning of the substituents represented by $R_3$ and/or $R_4$ is specified numerically, the link of the ring to the rest of the molecule being the 1-postion. Where two or more substituents are involved, each position is identified.

| Compound No. | $R_1$ | $R_2$ | $R_3$ | $R_4$ |
|---|---|---|---|---|
| 30) | H | $C_2H_5$ | 4-$OCH_3$ | O<br>‖<br>2,6-$CH_3$, 4-$SCH_3$ |
| 31) | H | $C_2H_5$ | 4-$OCH_3$ | O<br>‖<br>2,6-$CH_3$, 4-$SCH_3$<br>‖<br>O |
| 32) | H | $C_2H_5$ | 4-$OCH_3$ | 2,6-$CH_3$, 4-$NO_2$ |
| 33) | H | $C_2H_5$ | H | 2,3,4,5,6-F |
| 34) | H | $C_2H_5$ | 4-$OCH_3$ | 4-$NO_2$ |
| 35) | H | $C_2H_5$ | 4-$OCH_3$ | 4-$SCH_3$ |
| 36) | H | $C_2H_5$ | 4-$OCH_3$ | O<br>‖<br>4-$SCH_3$ |
| 37) | H | $C_2H_5$ | 4-$OCH_3$ | O<br>‖<br>4-$SCH_3$<br>‖<br>O |
| 38) | H | $C_2H_5$ | 4-$OC_2H_5$ | 4-$SCH_3$ |
| 39) | H | $C_2H_5$ | 4-$OC_2H_5$ | O<br>‖<br>4-$SCH_3$ |
| 40) | H | $C_2H_5$ | 4-$OC_2H_5$ | O<br>‖<br>4-$SCH_3$<br>‖<br>O |
| 41) | H | $C_2H_5$ | 4-$OC_2H_5$ | 4-$NO_2$ |
| 42) | H | $C_2H_5$ | 4-$OC_4H_9$ | 4-$SCH_3$ |
| 43) | H | $C_2H_5$ | 4-$OC_4H_9$ | O<br>‖<br>4-$SCH_3$ |
| 44) | H | $C_2H_5$ | 4-$OC_4H_9$ | O<br>‖<br>4-$SCH_3$<br>‖<br>O |
| 45) | H | $C_2H_5$ | 3,4,5-$OCH_3$ | 4-$SCH_3$ |
| 46) | H | $C_2H_5$ | 3,4,5-$OCH_3$ | O<br>‖<br>4-$SCH_3$ |
| 47) | H | $C_2H_5$ | 3,4,5-$OCH_3$ | O<br>‖<br>4-$SCH_3$<br>‖<br>O |
| 48) | H | $C_2H_5$ | 3,4-$OCH_3$ | 4-$SCH_3$ |
| 49) | H | $C_2H_5$ | 3,4-$OCH_3$ | O<br>‖<br>4-$SCH_3$ |
| 50) | H | $C_2H_5$ | 3,4-$OCH_3$ | O<br>‖<br>4-$SCH_3$<br>‖<br>O |
| 51) | H | $C_2H_5$ | 3,4-$OCH_3$ | 4-$NO_2$ |
| 52) | H | $C_2H_5$ | 4-OH | 4-$SCH_3$ |

TABLE I-continued

This table exemplifies compounds of the formula (VI) wherein $R_1$-$R_4$ have the values indicated. Positioning of the substituents represented by $R_3$ and/or $R_4$ is specified numerically, the link of the ring to the rest of the molecule being the 1-postion. Where two or more substituents are involved, each position is identified.

| Compound No. | $R_1$ | $R_2$ | $R_3$ | $R_4$ |
|---|---|---|---|---|
| 53) | H | $C_2H_5$ | 4-OH | O<br>‖<br>4-$SCH_3$ |
| 54) | H | $C_2H_5$ | 4-OH | O<br>‖<br>4-$SCH_3$<br>‖<br>O |
| 55) | H | $C_2H_5$ | 4-OH | 4-$NO_2$ |
| 56) | H | $C_2H_5$ | 3-OH | 4-$SCH_3$ |
| 57) | H | $C_2H_5$ | 3-OH | O<br>‖<br>4-$SCH_3$ |
| 58) | H | $C_2H_5$ | 3-OH | O<br>‖<br>4-$SCH_3$<br>‖<br>O |
| 59) | H | $C_2H_5$ | 3-OH | 4-$NO_2$ |
| 60) | H | $C_2H_5$ | 3-$OCH_3$ | 4-$SCH_3$ |
| 61) | H | $C_2H_5$ | 3-$OCH_3$ | O<br>‖<br>4-$SCH_3$ |
| 62) | H | $C_2H_5$ | 3-$OCH_3$ | O<br>‖<br>4-$SCH_3$<br>‖<br>O |
| 63) | H | $C_2H_5$ | 3-$OCH_3$ | 4-$NO_2$ |
| 64) | H | $C_2H_5$ | 4-$OC_9H_{19}$ | 4-$SCH_3$ |
| 65) | H | $C_2H_5$ | 4-$OC_9H_{19}$ | O<br>‖<br>4-$SCH_3$ |
| 66) | H | $C_2H_5$ | 4-$OC_9H_{19}$ | O<br>‖<br>4-$SCH_3$<br>‖<br>O |
| 67) | H | $C_2H_5$ | 4-$OC_9H_{19}$ | 4-$NO_2$ |
| 68) | H | $C_2H_5$ | 4-$OCH_2CO_2C_2H_5$ | 4-$SCH_3$ |
| 69) | H | $C_2H_5$ | 4-$OCH_2CO_2C_2H_5$ | O<br>‖<br>4-$SCH_3$ |
| 70) | H | $C_2H_5$ | 4-$OCH_2CO_2C_2H_5$ | O<br>‖<br>4-$SCH_3$<br>‖<br>O |
| 71) | H | $C_2H_5$ | 4-$OCH_2CO_2C_2H_5$ | 4-$NO_2$ |
| 72) | H | n-$C_3H_7$ | 4-$OCH_3$ | 4-$SCH_3$ |
| 73) | H | n-$C_3H_7$ | 4-$OCH_3$ | O<br>‖<br>4-$SCH_3$ |
| 74) | H | n-$C_3H_7$ | 4-$OCH_3$ | O<br>‖<br>4-$SCH_3$<br>‖<br>O |
| 75 | H | n-$C_3H_7$ | 4-$OCH_3$ | 4-$NO_2$ |
| 76) | H | n-$C_4H_9$ | 4-$OCH_3$ | 4-$SCH_3$ |

TABLE I-continued

This table exemplifies compounds of the formula (VI) wherein $R_1$-$R_4$ have the values indicated. Positioning of the substituents represented by $R_3$ and/or $R_4$ is specified numerically, the link of the ring to the rest of the molecule being the 1-postion. Where two or more substituents are involved, each position is identified.

| Compound No. | $R_1$ | $R_2$ | $R_3$ | $R_4$ |
|---|---|---|---|---|
| 77) | H | n-$C_4H_9$ | 4-$OCH_3$ | O<br>‖<br>4-$SCH_3$ |
| 78) | H | n-$C_4H_9$ | 4-$OCH_3$ | O<br>‖<br>4-$SCH_3$<br>‖<br>O |
| 79) | H | n-$C_4H_9$ | 4-$OCH_3$ | 4-$NO_2$ |
| 80) | H | $C_2H_5$ | 3-$OCH_3$,<br>4-$OC_2H_5$ | 4-$SCH_3$ |
| 81) | H | $C_2H_5$ | 3-$OCH_3$,<br>4-$OC_2H_5$ | O<br>‖<br>4-$SCH_3$ |
| 82) | H | $C_2H_5$ | 3-$OCH_3$,<br>4-$OC_2H_5$ | O<br>‖<br>4-$SCH_3$<br>‖<br>O |
| 83) | H | $C_2H_5$ | 3-$OCH_3$,<br>4-$OC_2H_5$ | 4-$NO_2$ |
| 84) | H | $C_2H_5$ | 3,5-$OCH_3$ | 4-$SCH_3$ |
| 85) | H | $C_2H_5$ | 3,5-$OCH_3$ | O<br>‖<br>4-$SCH_3$ |
| 86) | H | $C_2H_5$ | 3,5-$OCH_3$ | O<br>‖<br>4-$SCH_3$<br>‖<br>O |
| 87) | H | $C_2H_5$ | 3,5-$OCH_3$ | 4-$NO_2$ |
| 88) | H | $C_2H_5$ | 3-$OC_2H_5$,<br>4-$OCH_3$ | 4-$SCH_3$ |
| 89) | H | $C_2H_5$ | 3-$OC_2H_5$,<br>4-$OCH_3$ | O<br>‖<br>4-$SCH_3$ |
| 90) | H | $C_2H_5$ | 3-$OC_2H_5$,<br>4-$OCH_3$ | O<br>‖<br>4-$SCH_3$<br>‖<br>O |
| 91) | H | $C_2H_5$ | 3-$OC_2H_5$,<br>4-$OCH_3$ | 4-$NO_2$ |
| 92) | H | $C_2H_5$ | 4-$OC_6H_5$ | 4-$SCH_3$ |
| 93) | H | $C_2H_5$ | 4-$OC_6H_5$ | O<br>‖<br>4-$SCH_3$ |
| 94) | H | $C_2H_5$ | 4-$OC_6H_5$ | O<br>‖<br>4-$SCH_3$<br>‖<br>O |
| 95) | H | $C_2H_5$ | 4-$OC_6H_5$ | 4-$NO_2$ |
| 96) | H | $C_2H_5$ | 3-$OC_6H_5$ | 4-$SCH_3$ |
| 97) | H | $C_2H_5$ | 3-$OC_6H_5$ | O<br>‖<br>4-$SCH_3$ |
| 98) | H | $C_2H_5$ | 3-$OC_6H_5$ | O<br>‖<br>4-$SCH_3$<br>‖<br>O |

TABLE I-continued

This table exemplifies compounds of the formula (VI) wherein $R_1$-$R_4$ have the values indicated. Positioning of the substituents represented by $R_3$ and/or $R_4$ is specified numerically, the link of the ring to the rest of the molecule being the 1-postion. Where two or more substituents are involved, each position is identified.

| Compound No. | $R_1$ | $R_2$ | $R_3$ | $R_4$ |
|---|---|---|---|---|
| 99) | H | $C_2H_5$ | 3-$OC_6H_5$ | 4-$NO_2$ |
| 100) | H | $C_2H_5$ | 4-$CH_3$ | 4-$SCH_3$ |
| 101) | H | $C_2H_5$ | 4-$CH_3$ | O<br>‖<br>4-$SCH_3$ |
| 102) | H | $C_2H_5$ | 4-$CH_3$ | O<br>‖<br>4-$SCH_3$<br>‖<br>O |
| 103) | H | $C_2H_5$ | 4-$CH_3$ | 4-$NO_2$ |
| 104) | H | $C_2H_5$ | 3-$CH_3$ | 4-$SCH_3$ |
| 105) | H | $C_2H_5$ | 3-$CH_3$ | O<br>‖<br>4-$SCH_3$ |
| 106) | H | $C_2H_5$ | 3-$CH_3$ | O<br>‖<br>4-$SCH_3$<br>‖<br>O |
| 107) | H | $C_2H_5$ | 3-$CH_3$ | 4-$NO_2$ |
| 108) | H | $C_2H_5$ | 3,4-$CH_3$ | 4-$SCH_3$ |
| 109) | H | $C_2H_5$ | 3,4-$CH_3$ | O<br>‖<br>4-$SCH_3$ |
| 110) | H | $C_2H_5$ | 3,4-$CH_3$ | O<br>‖<br>4-$SCH_3$<br>‖<br>O |
| 111) | H | $C_2H_5$ | 3,4-$CH_3$ | 4-$NO_2$ |
| 112) | H | $C_2H_5$ | 3,4-$C_2H_5$ | 4-$SCH_3$ |
| 113) | H | $C_2H_5$ | 3,4-$C_2H_5$ | O<br>‖<br>4-$SCH_3$ |
| 114) | H | $C_2H_5$ | 3,4-$C_2H_5$ | O<br>‖<br>4-$SCH_3$<br>‖<br>O |
| 115) | H | $C_2H_5$ | 3,4-$C_2H_5$ | 4-$NO_2$ |
| 116) | H | $C_2H_5$ | 4-$C_2H_5$ | 4-$SCH_3$ |
| 117) | H | $C_2H_5$ | 4-$C_2H_5$ | O<br>‖<br>4-$SCH_3$ |
| 118) | H | $C_2H_5$ | 4-$C_2H_5$ | O<br>‖<br>4-$SCH_3$<br>‖<br>O |
| 119) | H | $C_2H_5$ | 4-$C_2H_5$ | 4-$NO_2$ |
| 120) | H | $C_2H_5$ | 4-$C_3H_7$ | 4-$SCH_3$ |
| 121) | H | $C_2H_5$ | 4-$C_3H_7$ | O<br>‖<br>4-$SCH_3$ |
| 122) | H | $C_2H_5$ | 4-$C_3H_7$ | O<br>‖<br>4-$SCH_3$<br>‖<br>O |

TABLE I-continued

This table exemplifies compounds of the formula (VI) wherein $R_1$–$R_4$ have the values indicated. Positioning of the substituents represented by $R_3$ and/or $R_4$ is specified numerically, the link of the ring to the rest of the molecule being the 1-postion. Where two or more substituents are involved, each position is identified.

| Compound No. | $R_1$ | $R_2$ | $R_3$ | $R_4$ |
|---|---|---|---|---|
| 123) | H | $C_2H_5$ | 4-$C_3H_7$ | 4-$NO_2$ |
| 124) | H | $C_2H_5$ | 4-$CH(CH_3)_2$ | 4-$SCH_3$ |
| 125) | H | $C_2H_5$ | 4-$CH(CH_3)_2$ | O<br>‖<br>4-$SCH_3$ |
| 126) | H | $C_2H_5$ | 4-$CH(CH_3)_2$ | O<br>‖<br>4-$SCH_3$<br>‖<br>O |
| 127) | H | $C_2H_5$ | 4-$CH(CH_3)_2$ | 4-$NO_2$ |
| 128) | H | $C_2H_5$ | 4-n-$C_4H_9$ | 4-$SCH_3$ |
| 129) | H | $C_2H_5$ | 4-n-$C_4H_9$ | O<br>‖<br>4-$SCH_3$ |
| 130) | H | $C_2H_5$ | 4-n-$C_4H_9$ | O<br>‖<br>4-$SCH_3$<br>‖<br>O |
| 131) | H | $C_2H_5$ | 4-n-$C_4H_9$ | 4-$NO_2$ |
| 132) | H | $CH_3$ | 4-$CH_2CH(CH_3)_2$ | 4-$SCH_3$ |
| 133) | H | $CH_3$ | 4-$CH_2CH(CH_3)_2$ | O<br>‖<br>4-$SCH_3$ |
| 134) | H | $CH_3$ | 4-$CH_2CH(CH_3)_2$ | O<br>‖<br>4-$SCH_3$<br>‖<br>O |
| 135) | H | $C_2H_5$ | 4-$CH_2CH(CH_3)_2$ | 4-$SCH_3$ |
| 136) | H | $C_2H_5$ | 4-$CH_2CH(CH_3)_2$ | O<br>‖<br>4-$SCH_3$ |
| 137) | H | $C_2H_5$ | 4-$CH_2CH(CH_3)_2$ | 4-$NO_2$ |
| 138) | H | $C_2H_5$ | 4-$CH_2CH(CH_3)_2$ | O<br>‖<br>4-$SCH_3$<br>‖<br>O |
| 139) | H | $C_2H_5$ | 4-$C(CH_3)_3$ | 4-$SCH_3$ |
| 140) | H | $C_2H_5$ | 4-$C(CH_3)_3$ | O<br>‖<br>4-$SCH_3$ |
| 141) | H | $C_2H_5$ | 4-$C(CH_3)_3$ | O<br>‖<br>4-$SCH_3$<br>‖<br>O |
| 142) | H | $C_2H_5$ | 4-$C(CH_3)_3$ | 4-$NO_2$ |
| 143) | H | $C_2H_5$ | 4-n-$C_5H_{11}$ | 4-$SCH_3$ |
| 144) | H | $C_2H_5$ | 4-n-$C_5H_{11}$ | O<br>‖<br>4-$SCH_3$ |
| 145) | H | $C_2H_5$ | 4-n-$C_5H_{11}$ | O<br>‖<br>4-$SCH_3$<br>‖<br>O |
| 146) | H | $C_2H_5$ | 4-n-$C_5H_{11}$ | 4-$NO_2$ |

TABLE I-continued

This table exemplifies compounds of the formula (VI) wherein $R_1$-$R_4$ have the values indicated. Positioning of the substituents represented by $R_3$ and/or $R_4$ is specified numerically, the link of the ring to the rest of the molecule being the 1-postion. Where two or more substituents are involved, each position is identified.

| Compound No. | $R_1$ | $R_2$ | $R_3$ | $R_4$ |
|---|---|---|---|---|
| 147) | H | $C_2H_5$ | 4-cyclohexyl | 4-$SCH_3$ |
| 148) | H | $C_2H_5$ | 4-cyclohexyl | O<br>\|\|<br>4-$SCH_3$ |
| 149) | H | $C_2H_5$ | 4-cyclohexyl | O<br>\|\|<br>4-$SCH_3$<br>\|\|<br>O |
| 150) | H | $C_2H_5$ | 4-cyclohexyl | 4-$NO_2$ |
| 151) | H | $C_2H_5$ | 4-cyclopropyl | 4-$SCH_3$ |
| 152) | H | $C_2H_5$ | 4-cyclopropyl | O<br>\|\|<br>4-$SCH_3$ |
| 153) | H | $C_2H_5$ | 4-cyclopropyl | O<br>\|\|<br>4-$SCH_3$<br>\|\|<br>O |
| 154) | H | $C_2H_5$ | 4-cyclopropyl | 4-$NO_2$ |
| 155) | H | $C_2H_5$ | 4-$SCH_3$ | 4-$SCH_3$ |
| 156) | H | $C_2H_5$ | 4-$SCH_3$ | O<br>\|\|<br>4-$SCH_3$ |
| 157) | H | $C_2H_5$ | 4-$SCH_3$ | O<br>\|\|<br>4-$SCH_3$<br>\|\|<br>O |
| 158) | H | $C_2H_5$ | 4-$SCH_3$ | 4-$NO_2$ |
| 159) | H | $C_2H_5$ | 4-$SC_2H_5$ | 4-$SCH_3$ |
| 160) | H | $C_2H_5$ | 4-$SC_2H_5$ | O<br>\|\|<br>4-$SCH_3$ |
| 161) | H | $C_2H_5$ | 4-$SC_2H_5$ | O<br>\|\|<br>4-$SCH_3$<br>\|\|<br>O |
| 162) | H | $C_2H_5$ | 4-$SC_2H_5$ | 4-$NO_2$ |
| 163) | H | $C_2H_5$ | O<br>\|\|<br>4-$SCH_3$<br>\|\|<br>O | 4-$SCH_3$ |
| 164) | H | $C_2H_5$ | O<br>\|\|<br>4-$SCH_3$<br>\|\|<br>O | O<br>\|\|<br>4-$SCH_3$ |
| 165) | H | $C_2H_5$ | O<br>\|\|<br>4-$SCH_3$<br>\|\|<br>O | O<br>\|\|<br>4-$SCH_3$<br>\|\|<br>O |
| 166) | H | $C_2H_5$ | 4-$N(CH_3)_2$ | 4-$SCH_3$ |
| 167) | H | $C_2H_5$ | 4-$N(CH_3)_2$ | O<br>\|\|<br>4-$SCH_3$ |

TABLE I-continued

This table exemplifies compounds of the formula (VI) wherein $R_1$-$R_4$ have the values indicated. Positioning of the substituents represented by $R_3$ and/or $R_4$ is specified numerically, the link of the ring to the rest of the molecule being the 1-postion. Where two or more substituents are involved, each position is identified.

| Compound No. | $R_1$ | $R_2$ | $R_3$ | $R_4$ |
|---|---|---|---|---|
| 168) | H | $C_2H_5$ | 4-$N(CH_3)_2$ | $4\text{-}\underset{\underset{O}{\|}}{\overset{\overset{O}{\|}}{S}}CH_3$ |
| 169) | H | $C_2H_5$ | 4-$N(CH_3)_2$ | 4-$NO_2$ |
| 170) | H | $C_2H_5$ | 4-$N(C_2H_5)_2$ | 4-$SCH_3$ |
| 171) | H | $C_2H_5$ | 4-$N(C_2H_5)_2$ | $4\text{-}\overset{\overset{O}{\|}}{S}CH_3$ |
| 172) | H | $C_2H_5$ | 4-$N(C_2H_5)_2$ | $4\text{-}\underset{\underset{O}{\|}}{\overset{\overset{O}{\|}}{S}}CH_3$ |
| 173) | H | $C_2H_5$ | 4-$N(C_2H_5)_2$ | 4-$NO_2$ |
| 174) | H | $C_2H_5$ | 3-$N(CH_3)_2$ | 4-$SCH_3$ |
| 175) | H | $C_2H_5$ | 3-$N(CH_3)_2$ | $4\text{-}\overset{\overset{O}{\|}}{S}CH_3$ |
| 176) | H | $C_2H_5$ | 3-$N(CH_3)_2$ | $4\text{-}\underset{\underset{O}{\|}}{\overset{\overset{O}{\|}}{S}}CH_3$ |
| 177) | H | $C_2H_5$ | 3-$N(CH_3)_2$ | 4-$NO_2$ |
| 178) | H | $C_2H_5$ | 4-$N_3$ | 4-$NO_2$ |
| 179) | H | $C_2H_5$ | 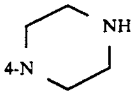 | 4-$SCH_3$ |
| 180) | H | $C_2H_5$ | 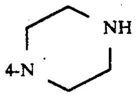 | $4\text{-}\overset{\overset{O}{\|}}{S}CH_3$ |
| 181) | H | $C_2H_5$ | 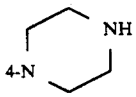 | $4\text{-}\underset{\underset{O}{\|}}{\overset{\overset{O}{\|}}{S}}CH_3$ |
| 182) | H | $C_2H_5$ | 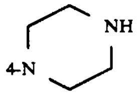 | 4-$NO_2$ |
| 183) | H | $C_2H_5$ | 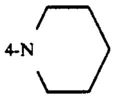 | 4-$SCH_3$ |
| 184 | H | $C_2H_5$ | 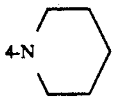 | $4\text{-}\overset{\overset{O}{\|}}{S}CH_3$ |
| 185) | H | $C_2H_5$ | 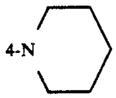 | $4\text{-}\underset{\underset{O}{\|}}{\overset{\overset{O}{\|}}{S}}CH_3$ |

TABLE I-continued

This table exemplifies compounds of the formula (VI) wherein $R_1$-$R_4$ have the values indicated. Positioning of the substituents represented by $R_3$ and/or $R_4$ is specified numerically, the link of the ring to the rest of the molecule being the 1-postion. Where two or more substituents are involved, each position is identified.

| Compound No. | $R_1$ | $R_2$ | $R_3$ | $R_4$ |
|---|---|---|---|---|
| 186) | H | $C_2H_5$ | 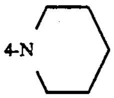 | 4-$NO_2$ |
| 187) | H | $C_2H_5$ | 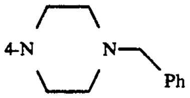 | 4-$SCH_3$ |
| 188) | H | $C_2H_5$ | 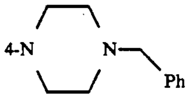 | O<br>‖<br>4-$SCH_3$ |
| 189) | H | $C_2H_5$ | 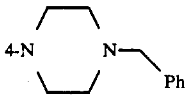 | O<br>‖<br>4-$SCH_3$<br>‖<br>O |
| 190) | H | $C_2H_5$ | 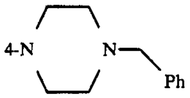 | 4-$NO_2$ |
| 191) | H | $C_2H_5$ | 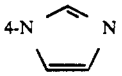 | 4-$SCH_3$ |
| 192) | H | $C_2H_5$ | 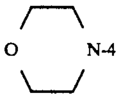 | O<br>‖<br>4-$SCH_3$ |
| 193) | H | $C_2H_5$ | 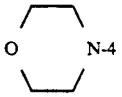 | O<br>‖<br>4-$SCH_3$<br>‖<br>O |
| 194) | H | $C_2H_5$ | 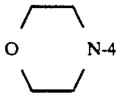 | 4-$NO_2$ |
| 195) | H | $C_2H_5$ | 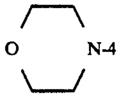 | 4-$SCH_3$ |
| 196) | H | $C_2H_5$ | 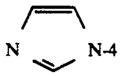 | O<br>‖<br>4-$SCH_3$ |
| 197) | H | $C_2H_5$ | 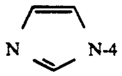 | O<br>‖<br>4-$SCH_3$<br>‖<br>O |
| 198) | H | $C_2H_5$ | 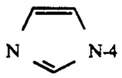 | 4-$NO_2$ |
| 199) | H | $C_2H_5$ | 4-F | 4-$SCH_3$ |

TABLE I-continued

This table exemplifies compounds of the formula (VI) wherein $R_1$-$R_4$ have the values indicated. Positioning of the substituents represented by $R_3$ and/or $R_4$ is specified numerically, the link of the ring to the rest of the molecule being the 1-postion. Where two or more substituents are involved, each position is identified.

| Compound No. | $R_1$ | $R_2$ | $R_3$ | $R_4$ |
|---|---|---|---|---|
| 200) | H | $C_2H_5$ | 4-F | 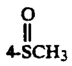 |
| 201) | H | $C_2H_5$ | 4-F | 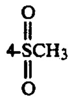 |
| 202) | H | $C_2H_5$ | 4-F | 4-$NO_2$ |
| 203) | H | $C_2H_5$ | 3-F | 4-$SCH_3$ |
| 204) | H | $C_2H_5$ | 3-F | 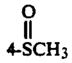 |
| 205) | H | $C_2H_5$ | 3-F | 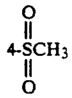 |
| 206) | H | $C_2H_5$ | 3-F | 4-$NO_2$ |
| 207) | H | $C_2H_5$ | 4-Cl | 4-$SCH_3$ |
| 208) | H | $C_2H_5$ | 4-Cl | 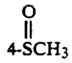 |
| 209) | H | $C_2H_5$ | 4-Cl | 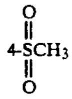 |
| 210) | H | $C_2H_5$ | 4-Cl | 4-$NO_2$ |
| 211) | H | $C_2H_5$ | 3-Cl | 4-$SCH_3$ |
| 212) | H | $C_2H_5$ | 3-Cl | 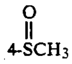 |
| 213) | H | $C_2H_5$ | 3-Cl | 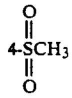 |
| 214) | H | $C_2H_5$ | 3-Cl | 4-$NO_2$ |
| 215) | H | $C_2H_5$ | 4-Br | 4-$SCH_3$ |
| 216) | H | $C_2H_5$ | 4-Br | 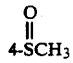 |
| 217) | H | $C_2H_5$ | 4-Br | 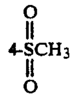 |
| 218) | H | $C_2H_5$ | 4-Br | 4-$NO_2$ |
| 219) | H | $C_2H_5$ | 3-Br | 4-$SCH_3$ |
| 220) | H | $C_2H_5$ | 3-Br | 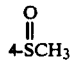 |
| 221) | H | $C_2H_5$ | 3-Br | 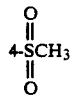 |
| 222) | H | $C_2H_5$ | 3-Br | 4-$NO_2$ |
| 223) | H | $C_2H_5$ | 4-$NHCOC_6H_5$ | 4-$SCH_3$ |

TABLE I-continued

This table exemplifies compounds of the formula (VI) wherein $R_1$-$R_4$ have the values indicated. Positioning of the substituents represented by $R_3$ and/or $R_4$ is specified numerically, the link of the ring to the rest of the molecule being the 1-postion. Where two or more substituents are involved, each position is identified.

| Compound No. | $R_1$ | $R_2$ | $R_3$ | $R_4$ |
|---|---|---|---|---|
| 224) | H | $C_2H_5$ | $4\text{-}NHCOC_6H_5$ | $4\text{-}\overset{\overset{O}{\|}}{S}CH_3$ |
| 225) | H | $C_2H_5$ | $4\text{-}NHCOC_6H_5$ | $4\text{-}\underset{\underset{O}{\|}}{\overset{\overset{O}{\|}}{S}}CH_3$ |
| 226) | H | $C_2H_5$ | $4\text{-}NHCOC_6H_5$ | $4\text{-}NO_2$ |
| 227) | H | $C_2H_5$ | $4\text{-}NH\overset{\overset{O}{\|}}{C}CH_2CH_2COOH$ | $4\text{-}SCH_3$ |
| 228) | H | $C_2H_5$ | $4\text{-}NH\overset{\overset{O}{\|}}{C}CH_2CH_2COOH$ | $4\text{-}\overset{\overset{O}{\|}}{S}CH_3$ |
| 229) | H | $C_2H_5$ | $4\text{-}NH\overset{\overset{O}{\|}}{C}CH_2CH_2COOH$ | $4\text{-}\underset{\underset{O}{\|}}{\overset{\overset{O}{\|}}{S}}CH_3$ |
| 230) | H | $C_2H_5$ | $4\text{-}NH\overset{\overset{O}{\|}}{C}CH_2CH_2COOH$ | $4\text{-}NO_2$ |
| 231) | H | $C_2H_5$ | $4\text{-}NH\overset{\overset{O}{\|}}{C}CH_2CH_2\overset{\overset{O}{\|}}{C}NHCH_2CH_2SO_3Na$ | $4\text{-}SCH_3$ |
| 232) | H | $C_2H_5$ | $4\text{-}NH\overset{\overset{O}{\|}}{C}CH_2CH_2\overset{\overset{O}{\|}}{C}NHCH_2CH_2SO_3Na$ | $4\text{-}\overset{\overset{O}{\|}}{S}CH_3$ |
| 233) | H | $C_2H_5$ | $4\text{-}NH\overset{\overset{O}{\|}}{C}CH_2CH_2\overset{\overset{O}{\|}}{C}NHCH_2CH_2SO_3Na$ | $4\text{-}\underset{\underset{O}{\|}}{\overset{\overset{O}{\|}}{S}}CH_3$ |
| 234) | H | $C_2H_5$ | 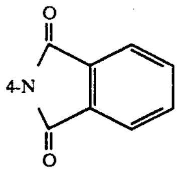 | $4\text{-}SCH_3$ |
| 235) | H | $C_2H_5$ | 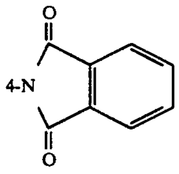 | $4\text{-}\overset{\overset{O}{\|}}{S}CH_3$ |
| 236) | H | $C_2H_5$ | 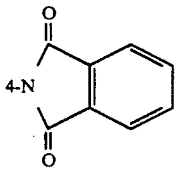 | $4\text{-}\underset{\underset{O}{\|}}{\overset{\overset{O}{\|}}{S}}CH_3$ |

TABLE I-continued

This table exemplifies compounds of the formula (VI) wherein $R_1$-$R_4$ have the values indicated. Positioning of the substituents represented by $R_3$ and/or $R_4$ is specified numerically, the link of the ring to the rest of the molecule being the 1-postion. Where two or more substituents are involved, each position is identified.

| Compound No. | $R_1$ | $R_2$ | $R_3$ | $R_4$ |
|---|---|---|---|---|
| 237) | H | $C_2H_5$ | 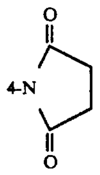 | $4\text{-}SCH_3$ |
| 238) | H | $C_2H_5$ | 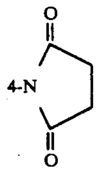 | O<br>‖<br>$4\text{-}SCH_3$ |
| 239) | H | $C_2H_5$ | 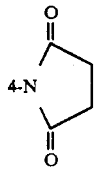 | O<br>‖<br>$4\text{-}SCH_3$<br>‖<br>O |
| 240 | H | $C_2H_5$ | $4\text{-}NH_2$ | $4\text{-}SCH_3$ |
| 241) | H | $C_2H_5$ | $4\text{-}NH_2$ | O<br>‖<br>$4\text{-}SCH_3$ |
| 242) | H | $C_2H_5$ | $4\text{-}NH_2$ | O<br>‖<br>$4\text{-}SCH_3$<br>‖<br>O |
| 243) | H | $C_2H_5$ | $4\text{-}NH_2$ | $4\text{-}NO_2$ |
| 244) | H | $C_2H_5$ | O O<br>‖ ‖<br>$4\text{-}NHCCH_2CH_2COCH_3$ | $4\text{-}SCH_3$ |
| 245) | H | $C_2H_5$ | O O<br>‖ ‖<br>$4\text{-}NHCCH_2CH_2COCH_3$ | O<br>‖<br>$4\text{-}SCH_2$ |
| 246) | H | $C_2H_5$ | O O<br>‖ ‖<br>$4\text{-}NHCCH_2CH_2COCH_3$ | O<br>‖<br>$4\text{-}SCH_3$<br>‖<br>O |
| 247) | H | $C_2H_5$ | O O<br>‖ ‖<br>$4\text{-}NHCCH_2CH_2COCH_3$ | $4\text{-}NO_2$ |
| 248) | H | $C_2H_5$ | O<br>‖<br>$4\text{-}NHCCH_3$ | $4\text{-}SCH_3$ |
| 249) | H | $C_2H_5$ | O<br>‖<br>$4\text{-}NHCCH_3$ | O<br>‖<br>$4\text{-}SCH_3$ |
| 250) | H | $C_2H_5$ | O<br>‖<br>$4\text{-}NHCCH_3$ | O<br>‖<br>$4\text{-}SCH_3$<br>‖<br>O |
| 251) | H | $C_2H_5$ | O<br>‖<br>$4\text{-}NHCCH_3$ | $4\text{-}NO_2$ |

TABLE I-continued

This table exemplifies compounds of the formula (VI) wherein $R_1$-$R_4$ have the values indicated. Positioning of the substituents represented by $R_3$ and/or $R_4$ is specified numerically, the link of the ring to the rest of the molecule being the 1-postion. Where two or more substituents are involved, each position is identified.

| Compound No. | $R_1$ | $R_2$ | $R_3$ | $R_4$ |
|---|---|---|---|---|
| 252) | H | $C_2H_5$ | O<br>‖<br>4-NHCC$_2$H$_5$ | 4-SCH$_3$ |
| 253) | H | $C_2H_5$ | O<br>‖<br>4-NHCC$_2$H$_5$ | O<br>‖<br>4-SCH$_3$ |
| 254) | H | $C_2H_5$ | O<br>‖<br>4-NHCC$_2$H$_5$ | O<br>‖<br>4-SCH$_3$<br>‖<br>O |
| 255) | H | $C_2H_5$ | O<br>‖<br>4-NHCC$_2$H$_5$ | 4-NO$_2$ |
| 256) | H | $C_2H_5$ | O<br>‖<br>4-NHCCH(CH$_3$)$_2$ | 4-SCH$_3$ |
| 257) | H | $C_2H_5$ | O<br>‖<br>4-NHCCH(CH$_3$)$_2$ | O<br>‖<br>4-SCH$_3$ |
| 258) | H | $C_2H_5$ | O<br>‖<br>4-NHCCH(CH$_3$)$_2$ | O<br>‖<br>4-SCH$_3$<br>‖<br>O |
| 259) | H | $C_2H_5$ | O<br>‖<br>4-NHCCH(CH$_3$)$_2$ | 4-NO$_2$ |
| 260) | H | $C_2H_5$ | O<br>‖<br>4-NHCC(CH$_3$)$_3$ | 4-SCH$_3$ |
| 261) | H | $C_2H_5$ | O<br>‖<br>4-NHCC(CH$_3$)$_3$ | O<br>‖<br>4-SCH$_3$ |
| 262) | H | $C_2H_5$ | O<br>‖<br>4-NHCC(CH$_3$)$_3$ | O<br>‖<br>4-SCH$_3$<br>‖<br>O |
| 263) | H | $C_2H_5$ | O<br>‖<br>4-NHCC(CH$_3$)$_3$ | 4-NO$_2$ |
| 264) | H | $C_2H_5$ | 4-C$_6$H$_5$ | 4-SCH$_3$ |
| 265) | H | $C_2H_5$ | 4-C$_6$H$_5$ | O<br>‖<br>4-SCH$_3$ |
| 266) | H | $C_2H_5$ | 4-C$_6$H$_5$ | O<br>‖<br>4-SCH$_3$<br>‖<br>O |
| 267) | H | $C_2H_5$ | 4-C$_6$H$_5$ | 4-NO$_2$ |
| 268) | $CH_3$ | $CH_3$ | H | 4-SCH$_3$ |
| 269) | $CH_3$ | $CH_3$ | H | O<br>‖<br>4-SCH$_3$ |
| 270) | $CH_3$ | $CH_3$ | H | O<br>‖<br>4-SCH$_3$<br>‖<br>O |

TABLE I-continued

This table exemplifies compounds of the formula (VI) wherein $R_1$-$R_4$ have the values indicated. Positioning of the substituents represented by $R_3$ and/or $R_4$ is specified numerically, the link of the ring to the rest of the molecule being the 1-postion. Where two or more substituents are involved, each position is identified.

| Compound No. | $R_1$ | $R_2$ | $R_3$ | $R_4$ |
|---|---|---|---|---|
| 271) | $CH_3$ | $CH_3$ | H | 4-$NO_2$ |
| 272) | $C_2H_5$ | $C_2H_5$ | H | 4-$SCH_3$ |
| 273) | $C_2H_5$ | $C_2H_5$ | H | O<br>‖<br>4-$SCH_3$ |
| 274) | $C_2H_5$ | $C_2H_5$ | H | O<br>‖<br>4-$SCH_3$<br>‖<br>O |
| 275) | $C_2H_5$ | $C_2H_5$ | H | 4-$NO_2$ |
| 276) | $(CH_2)_2$ | | H | 4-$SCH_3$ |
| 277) | $(CH_2)_2$ | | H | O<br>‖<br>4-$SCH_3$ |
| 278) | $(CH_2)_2$ | | H | O<br>‖<br>4-$SCH_3$<br>‖<br>O |
| 279) | $(CH_2)_2$ | | H | 4-$NO_2$ |
| 280) | $(CH_2)_3$ | | H | 4-$SCH_3$ |
| 281) | $(CH_2)_3$ | | H | O<br>‖<br>4-$SCH_3$ |
| 282) | $(CH_2)_3$ | | H | O<br>‖<br>4-$SCH_3$<br>‖<br>O |
| 283) | $(CH_2)_3$ | | H | 4-$NO_2$ |
| 284) | $(CH_2)_4$ | | H | 4-$SCH_3$ |
| 285) | $(CH_2)_4$ | | H | O<br>‖<br>4-$SCH_3$ |
| 286) | $(CH_2)_4$ | | H | O<br>‖<br>4-$SCH_3$<br>‖<br>O |
| 287) | $(CH_2)_4$ | | H | 4-$NO_2$ |
| 288) | $CH_3$ | $CH_3$ | 4-$OCH_3$ | 4-$SCH_3$ |
| 289) | $CH_3$ | $CH_3$ | 4-$OCH_3$ | O<br>‖<br>4-$SCH_3$ |
| 290) | $CH_3$ | $CH_3$ | 4-$OCH_3$ | O<br>‖<br>4-$SCH_3$<br>‖<br>O |
| 291) | $CH_3$ | $CH_3$ | 4-$OCH_3$ | 4-$NO_2$ |
| 292) | $C_2H_5$ | $C_2H_5$ | 4-$OCH_3$ | 4-$SCH_3$ |
| 293) | $C_2H_5$ | $C_2H_5$ | 4-$OCH_3$ | O<br>‖<br>4-$SCH_3$ |
| 294) | $C_2H_5$ | $C_2H_5$ | 4-$OCH_3$ | O<br>‖<br>4-$SCH_3$<br>‖<br>O |

TABLE I-continued

This table exemplifies compounds of the formula (VI) wherein $R_1$-$R_4$ have the values indicated. Positioning of the substituents represented by $R_3$ and/or $R_4$ is specified numerically, the link of the ring to the rest of the molecule being the 1-postion. Where two or more substituents are involved, each position is identified.

| Compound No. | $R_1$ | $R_2$ | $R_3$ | $R_4$ |
|---|---|---|---|---|
| 295) | $C_2H_5$ | $C_2H_5$ | 4-$OCH_3$ | 4-$NO_2$ |
| 296) | $(CH_2)_2$ | | 4-$OCH_3$ | 4-$SCH_3$ |
| 297) | $(CH_2)_2$ | | 4-$OCH_3$ | O<br>‖<br>4-$SCH_3$ |
| 298) | $(CH_2)_2$ | | 4-$OCH_3$ | O<br>‖<br>4-$SCH_3$<br>‖<br>O |
| 299) | $(CH_2)_2$ | | 4-$OCH_3$ | 4-$NO_2$ |
| 300) | $(CH_2)_3$ | | 4-$OCH_3$ | 4-$SCH_3$ |
| 301) | $(CH_2)_3$ | | 4-$OCH_3$ | O<br>‖<br>4-$SCH_3$ |
| 302) | $(CH_2)_3$ | | 4-$OCH_3$ | O<br>‖<br>4-$SCH_3$<br>‖<br>O |
| 303) | $(CH_2)_3$ | | 4-$OCH_3$ | 4-$NO_2$ |
| 304) | $(CH_2)_4$ | | 4-$OCH_3$ | 4-$SCH_3$ |
| 305) | $(CH_2)_4$ | | 4-$OCH_3$ | O<br>‖<br>4-$SCH_3$ |
| 306) | $(CH_2)_4$ | | 4-$OCH_3$ | O<br>‖<br>4-$SCH_3$<br>‖<br>O |
| 307 | $(CH_2)_4$ | | 4-$OCH_3$ | 4-$NO_2$ |
| 308) | $CH_3$ | $CH_3$ | 4-$OCH_3$ | 4-$SCH_2C(CH_3)_2CO_2H$ |
| 309) | $CH_3$ | $CH_3$ | 4-$OCH_3$ | O<br>‖<br>4-$SCH_2C(CH_3)_2CO_2H$ |
| 310) | $CH_3$ | $CH_3$ | 4-$OCH_3$ | O<br>‖<br>4-$SCH_2C(CH_3)_2CO_2H$<br>‖<br>O |
| 311) | $(CH_2)_3$ | | 4-$OCH_3$ | 4-$SCH_2C(CH_3)_2CO_2H$ |
| 312) | $(CH_2)_3$ | | 4-$OCH_3$ | O<br>‖<br>4-$SCH_2C(CH_3)_2CO_2H$ |
| 313) | $(CH_2)_3$ | | 4-$OCH_3$ | O<br>‖<br>4-$SCH_2C(CH_3)_2CO_2H$<br>‖<br>O |
| 314) | $CH_3$ | $CH_3$ | H | 4-$SCH_2C(CH_3)_2CO_2H$ |
| 315) | $CH_3$ | $CH_3$ | H | O<br>‖<br>4-$SCH_2C(CH_3)_2CO_2H$ |
| 316) | $CH_3$ | $CH_3$ | H | O<br>‖<br>4-$SCH_2C(CH_3)_2CO_2H$<br>‖<br>O |
| 317) | $(CH_2)_3$ | | H | 4-$SCH_2C(CH_3)_2CO_2H$ |

TABLE I-continued

This table exemplifies compounds of the formula (VI) wherein $R_1$-$R_4$ have the values indicated. Positioning of the substituents represented by $R_3$ and/or $R_4$ is specified numerically, the link of the ring to the rest of the molecule being the 1-postion. Where two or more substituents are involved, each position is identified.

| Compound No. | $R_1$ | $R_2$ | $R_3$ | $R_4$ |
|---|---|---|---|---|
| 318) | $(CH_2)_3$ | | H | O<br>‖<br>4-$SCH_2C(CH_3)_2CO_2H$ |
| 319) | $(CH_2)_3$ | | H | O<br>‖<br>4-$SCH_2C(CH_3)_2CO_2H$<br>‖<br>O |
| 320) | $C_2H_5$ | $C_2H_5$ | H | 4-$SCH_2C(CH_3)_2CO_2H$ |
| 321) | $C_2H_5$ | $C_2H_5$ | H | O<br>‖<br>4-$SCH_2C(CH_3)_2CO_2H$ |
| 322) | $C_2H_5$ | $C_2H_5$ | H | O<br>‖<br>4-$SCH_2C(CH_3)_2CO_2H$<br>‖<br>O |
| 323) | H | $C_2H_5$ | H | 4-$SCH_2C(CH_3)_2CO_2H$ |
| 324) | H | $C_2H_5$ | H | O<br>‖<br>4-$SCH_2C(CH_3)_2CO_2H$ |
| 325) | H | $C_2H_5$ | H | O<br>‖<br>4-$SCH_2C(CH_3)_2CO_2H$<br>‖<br>O |
| 326) | H | $C_2H_5$ | 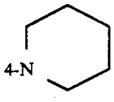 | 4-$SCH_2C(CH_3)_2CO_2H$ |
| 327) | H | $C_2H_5$ | 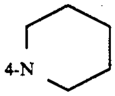 | O<br>‖<br>4-$SCH_2C(CH_3)_2CO_2H$ |
| 328) | H | $C_2H_5$ | 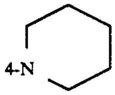 | O<br>‖<br>4-$SCH_2C(CH_3)_2CO_2H$<br>‖<br>O |
| 329) | H | $C_2H_5$ | 4-cyclohexyl | 4-$SCH_2C(CH_3)_2CO_2H$ |
| 330) | H | $C_2H_5$ | 4-cyclohexyl | O<br>‖<br>4-$SCH_2C(CH_3)_2CO_2H$ |
| 331) | H | $C_2H_5$ | 4-cyclohexyl | O<br>‖<br>4-$SCH_2C(CH_3)_2CO_2H$<br>‖<br>O |
| 332) | H | $C_2H_5$ | 4-$C_2H_5$ | 4-$SCH_2C(CH_3)_2CO_2H$ |
| 333) | H | $C_2H_5$ | 4-$C_2H_5$ | O<br>‖<br>4-$SCH_2C(CH_3)_2CO_2H$ |
| 334) | H | $C_2H_5$ | 4-$C_2H_5$ | O<br>‖<br>4-$SCH_2C(CH_3)_2CO_2H$<br>‖<br>O |
| 335) | H | $C_2H_5$ | 3,4-$C_2H_5$ | 4-$SCH_2C(CH_3)_2CO_2H$ |

TABLE I-continued

This table exemplifies compounds of the formula (VI) wherein $R_1$-$R_4$ have the values indicated. Positioning of the substituents represented by $R_3$ and/or $R_4$ is specified numerically, the link of the ring to the rest of the molecule being the 1-postion. Where two or more substituents are involved, each position is identified.

| Compound No. | $R_1$ | $R_2$ | $R_3$ | $R_4$ |
|---|---|---|---|---|
| 336) | H | $C_2H_5$ | 3,4-$C_2H_5$ | O<br>\|\|<br>4-$SCH_2C(CH_3)_2CO_2H$ |
| 337) | H | $C_2H_5$ | 3,4-$C_2H_5$ | O<br>\|\|<br>4-$SCH_2C(CH_3)_2CO_2H$<br>\|\|<br>O |
| 338) | H | $C_2H_5$ | 4-$NHCOC_6H_5$ | 4-$SCH_2C(CH_3)_2CO_2H$ |
| 339) | H | $C_2H_5$ | 4-$NHCOC_6H_5$ | O<br>\|\|<br>4-$SCH_2C(CH_3)_2CO_2H$ |
| 340) | H | $C_2H_5$ | 4-$NHCOC_6H_5$ | O<br>\|\|<br>4-$SCH_2C(CH_3)_2CO_2H$<br>\|\|<br>O |
| 341) | $CH_3$ | $CH_3$ | 3,4-$C_2H_5$ | 4-$SCH_2C(CH_3)_2CO_2H$ |
| 342) | $CH_3$ | $CH_3$ | 3,4-$C_2H_5$ | O<br>\|\|<br>4-$SCH_2C(CH_3)_2CO_2H$ |
| 343) | $CH_3$ | $CH_3$ | 3,4-$C_2H_5$ | O<br>\|\|<br>4-$SCH_2C(CH_3)_2CO_2H$<br>\|\|<br>O |
| 344) | $(CH_2)_3$ | | 3,4-$C_2H_5$ | 4-$SCH_2C(CH_3)_2CO_2H$ |
| 345) | $(CH_2)_3$ | | 3,4-$C_2H_5$ | O<br>\|\|<br>4-$SCH_2C(CH_3)_2CO_2H$ |
| 346) | $(CH_2)_3$ | | 3,4-$C_2H_5$ | O<br>\|\|<br>4-$SCH_2C(CH_3)_2CO_2H$<br>\|\|<br>O |
| 347) | $CH_3$ | $CH_3$ | 4-cyclohexyl | 4-$SCH_2C(CH_3)_2CO_2H$ |
| 348) | $CH_3$ | $CH_3$ | 4-cyclohexyl | O<br>\|\|<br>4-$SCH_2C(CH_3)_2CO_2H$ |
| 349) | $CH_3$ | $CH_3$ | 4-cyclohexyl | O<br>\|\|<br>4-$SCH_2C(CH_3)_2CO_2H$<br>\|\|<br>O |
| 350) | $(CH_2)_3$ | | 4-cyclohexyl | 4-$SCH_2C(CH_3)_2CO_2H$ |
| 351) | $(CH_2)_3$ | | 4-cyclohexyl | O<br>\|\|<br>4-$SCH_2C(CH_3)_2CO_2H$ |
| 352) | $(CH_2)_3$ | | 4-cyclohexyl | O<br>\|\|<br>4-$SCH_2C(CH_3)_2CO_2H$<br>\|\|<br>O |
| 353) | $CH_3$ | $CH_3$ | 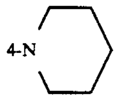 | 4-$SCH_2C(CH_3)_2CO_2H$ |

TABLE I-continued

This table exemplifies compounds of the formula (VI) wherein $R_1$-$R_4$ have the values indicated. Positioning of the substituents represented by $R_3$ and/or $R_4$ is specified numerically, the link of the ring to the rest of the molecule being the 1-postion. Where two or more substituents are involved, each position is identified.

| Compound No. | $R_1$ | $R_2$ | $R_3$ | $R_4$ |
|---|---|---|---|---|
| 354) | $CH_3$ | $CH_3$ | 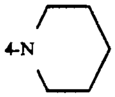 | O<br>‖<br>4-$SCH_2C(CH_3)_2CO_2H$ |
| 355) | $CH_3$ | $CH_3$ | 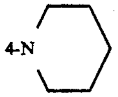 | O<br>‖<br>4-$SCH_2C(CH_3)_2CO_2H$<br>‖<br>O |
| 356) | $(CH_2)_3$ | | 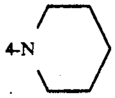 | 4-$SCH_2C(CH_3)_2CO_2H$ |
| 357) | $(CH_2)_3$ | | 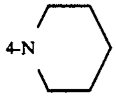 | O<br>‖<br>4-$SCH_2C(CH_3)_2CO_2H$ |
| 358) | $(CH_2)_3$ | | 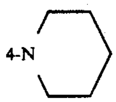 | O<br>‖<br>4-$SCH_2C(CH_3)_2CO_2H$<br>‖<br>O |

TABLE II

Other compounds contemplated herein include the following compounds of formula (X):

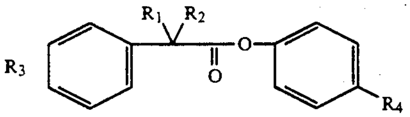

(X)

| Compound No. | $R_1$ | $R_2$ | $R_3$ | $R_4$ |
|---|---|---|---|---|
| 359) | H | $C_2H_5$ | 3-$(CH_2)_3$-4 | 4-$SCH_3$ |
| 360) | H | $C_2H_5$ | 3-$(CH_2)_3$-4 | O<br>‖<br>4-$SCH_3$ |
| 361) | H | $C_2H_5$ | 3-$(CH_2)_3$-4 | O<br>‖<br>4-$SCH_3$<br>‖<br>O |
| 362) | H | $C_2H_5$ | 3-$(CH_2)_3$-4 | 4-$NO_2$ |
| 363) | H | $C_2H_5$ | 3-$(CH_2)_4$-4 | 4-$SCH_3$ |
| 364) | H | $C_2H_5$ | 3-$(CH_2)_4$-4 | O<br>‖<br>4-$SCH_3$ |
| 365) | H | $C_2H_5$ | 3-$(CH_2)_4$-4 | O<br>‖<br>4-$SCH_3$<br>‖<br>O |
| 366) | H | $C_2H_5$ | 3-$(CH_2)_4$-4 | 4-$NO_2$ |
| 367) | H | $C_2H_5$ | 3-$OCH_2CH_2O$-4 | 4-$SCH_3$ |
| 368) | H | $C_2H_5$ | 3-$OCH_2CH_2O$-4 | O<br>‖<br>4-$SCH_3$ |

TABLE II-continued

Other compounds contemplated herein include the following compounds of formula (X):

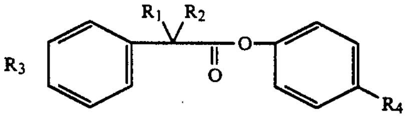

(X)

| Compound No. | $R_1$ | $R_2$ | $R_3$ | $R_4$ |
|---|---|---|---|---|
| 369) | H | $C_2H_5$ | 3-$OCH_2CH_2O$-4 | $4\text{-}\underset{\underset{O}{\|}}{\overset{\overset{O}{\|}}{S}}CH_3$ |
| 370) | H | $C_2H_5$ | 3-$OCH_2CH_2O$-4 | 4-$NO_2$ |
| 371) | H | $C_2H_5$ | 3-$OCH_2O$-4 | 4-$SCH_3$ |
| 372) | H | $C_2H_5$ | 3-$OCH_2O$-4 | $4\text{-}\overset{\overset{O}{\|}}{S}CH_3$ |
| 373) | H | $C_2H_5$ | 3-$OCH_2O$-4 | $4\text{-}\underset{\underset{O}{\|}}{\overset{\overset{O}{\|}}{S}}CH_3$ |
| 374) | H | $C_2H_5$ | 3-$OCH_2O$-4 | 4-$NO_2$ |
| 375) (+) | H | $CH_3$ | 3-CHCHC($OCH_3$)CH-4 | 4-$SCH_3$ |
| 376) (+) | H | $CH_3$ | 3-CHCHC($OCH_3$)CH-4 | $4\text{-}\overset{\overset{O}{\|}}{S}CH_3$ |
| 377) (+) | H | $CH_3$ | 3-CHCHC($OCH_3$)CH-4 | $4\text{-}\underset{\underset{O}{\|}}{\overset{\overset{O}{\|}}{S}}CH_3$ |
| 378) (+/−) | H | $CH_3$ | 3-CHCHC($OCH_3$)CH-4 | 4-$SCH_3$ |
| 379) (+/−) | H | $CH_3$ | 3-CHCHC($OCH_3$)CH-4 | $4\text{-}\overset{\overset{O}{\|}}{S}CH_3$ |
| 380) (+/−) | H | $CH_3$ | 3-CHCHC($OCH_3$)CH-4 | $4\text{-}\underset{\underset{O}{\|}}{\overset{\overset{O}{\|}}{S}}CH_3$ |
| 381) (+/−) | H | $CH_3$ | 3-CHCHC($OCH_3$)CH-4 | 4-$NO_2$ |
| 382) (+/−) | H | $C_2H_5$ | 3-CHCHC($OCH_3$)CH-4 | 4-$SCH_3$ |
| 383) (+/−) | H | $C_2H_5$ | 3-CHCHC($OCH_3$)CH-4 | $4\text{-}\overset{\overset{O}{\|}}{S}CH_3$ |
| 384) (+/−) | H | $C_2H_5$ | 3-CHCHC($OCH_3$)CH-4 | $4\text{-}\underset{\underset{O}{\|}}{\overset{\overset{O}{\|}}{S}}CH_3$ |
| 385) (+/−) | H | $C_2H_5$ | 3-CHCHC($OCH_3$)CH-4 | 4-$NO_2$ |
| 386) (+/−) | H | $C_2H_5$ | 3-CHCHC($OCH_3$)CH-4 | 4-$SCH_2C(CH_3)_2CO_2H$ |
| 387) (+/−) | H | $C_2H_5$ | 3-CHCHC($OCH_3$)CH-4 | $4\text{-}\overset{\overset{O}{\|}}{S}CH_2C(CH_3)_2CO_2H$ |
| 388) (+/−) | H | $C_2H_5$ | 3-CHCHC($OCH_3$)CH-4 | $4\text{-}\underset{\underset{O}{\|}}{\overset{\overset{O}{\|}}{S}}CH_2C(CH_3)_2CO_2H$ |
| 389) | H | $C_2H_5$ | 3-$(CH_2)_4$-4 | 4-$SCH_2C(CH_3)_2CO_2H$ |
| 390) | H | $C_2H_5$ | 3-$(CH_2)_4$-4 | $4\text{-}\overset{\overset{O}{\|}}{S}CH_2C(CH_3)_2CO_2H$ |

TABLE II-continued

Other compounds contemplated herein include the following compounds of formula (X):

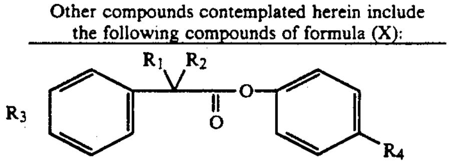

(X)

| Compound No. | $R_1$ | $R_2$ | $R_3$ | $R_4$ |
|---|---|---|---|---|
| 391) | H | $C_2H_5$ | 3-$(CH_2)_4$-4 | O<br>‖<br>4-$SCH_2C(CH_3)_2CO_2H$<br>‖<br>O |
| 392) | $CH_3$ | $CH_3$ | 3-$(CH_2)_4$-4 | 4-$SCH_2C(CH_3)_2CO_2H$ |
| 393) | $CH_3$ | $CH_3$ | 3-$(CH_2)_4$-4 | O<br>‖<br>4-$SCH_2C(CH_3)_2CO_2H$ |
| 394) | $CH_3$ | $CH_3$ | 3-$(CH_2)_4$-4 | O<br>‖<br>4-$SCH_2C(CH_3)_2CO_2H$<br>‖<br>O |
| 395) | $(CH_2)_3$ | | 3-$(CH_2)_4$-4 | 4-$SCH_2C(CH_3)_2CO_2H$ |
| 396) | $(CH_2)_3$ | | 3-$(CH_2)_4$-4 | O<br>‖<br>4-$SCH_2C(CH_3)_2CO_2H$ |
| 397) | $(CH_2)_3$ | | 3-$(CH_2)_4$-4 | O<br>‖<br>4-$SCH_2C(CH_3)_2CO_2H$<br>‖<br>O |

Broadly described, the products of the invention may be prepared by procedures available to those in the art. A representative synthesis procedure may be illustrated by the following Reaction Schemes A-E:

Reaction Scheme A
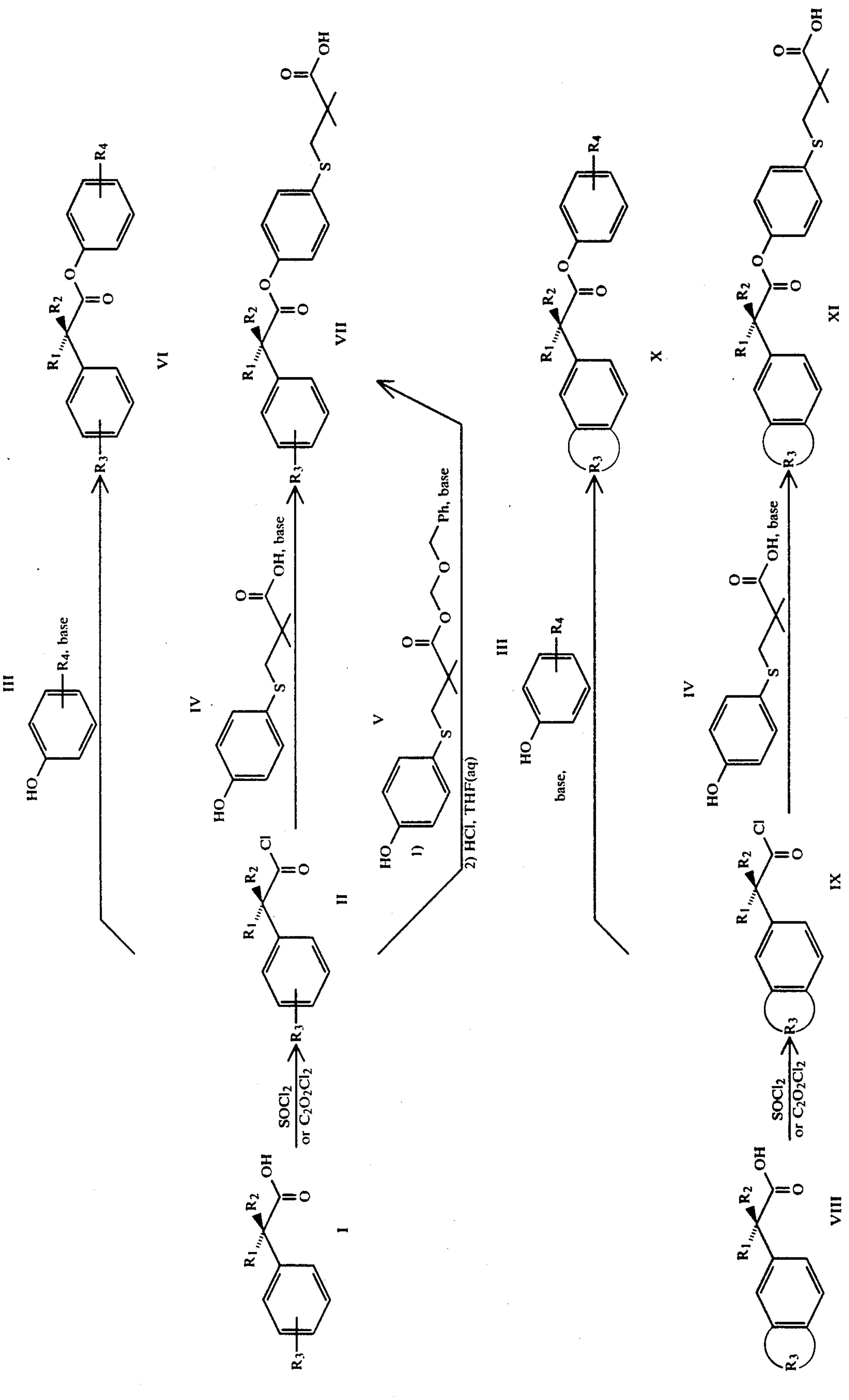
I II III IV V VI VII VIII IX III X IV XI

-continued
Reaction Scheme A
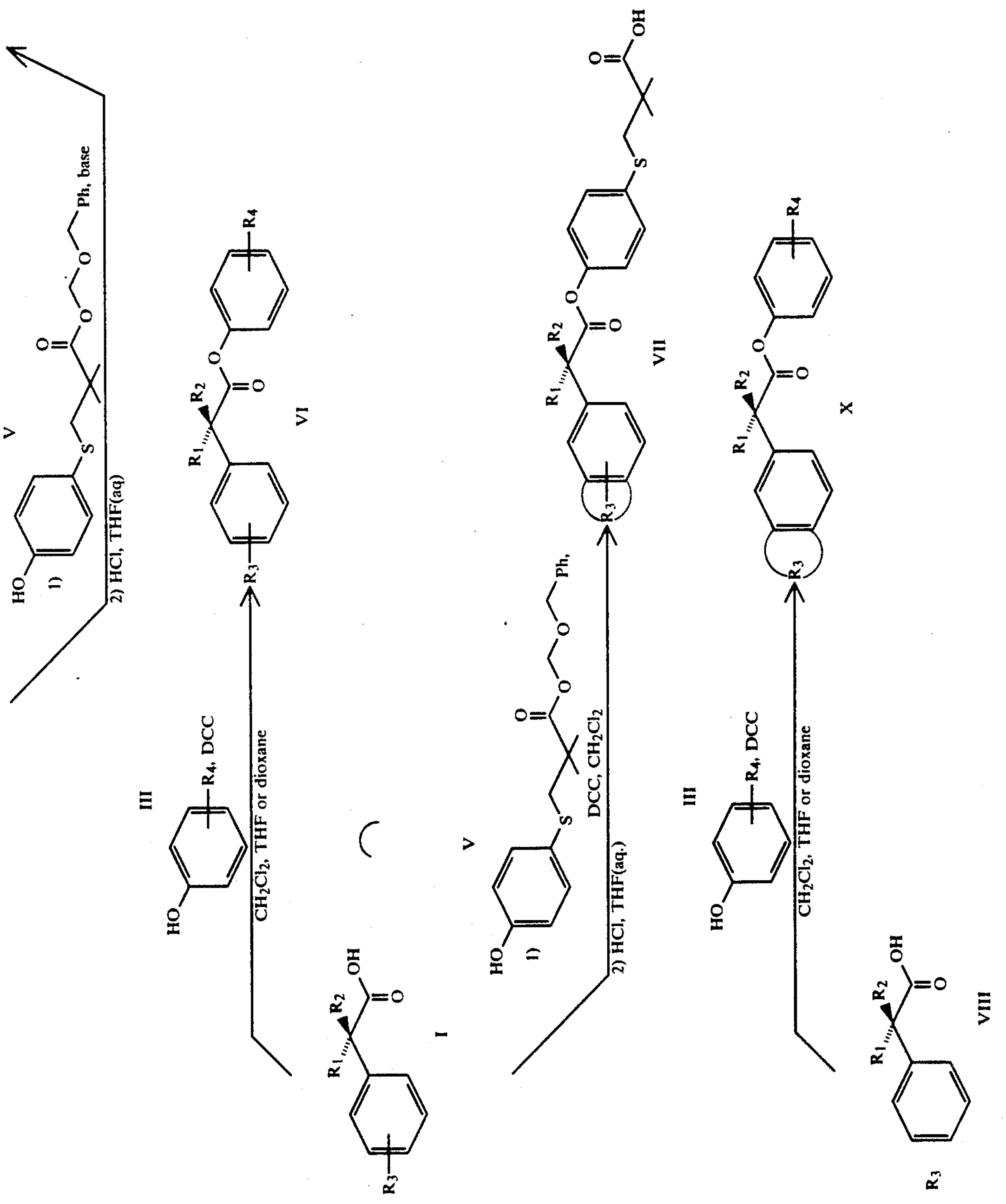

-continued
Reaction Scheme A
V
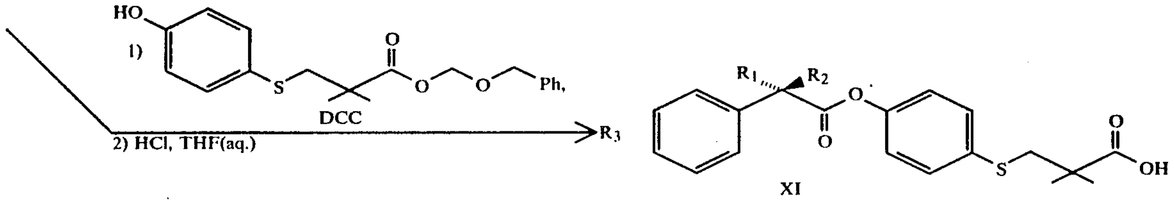
XI

Reaction Scheme B
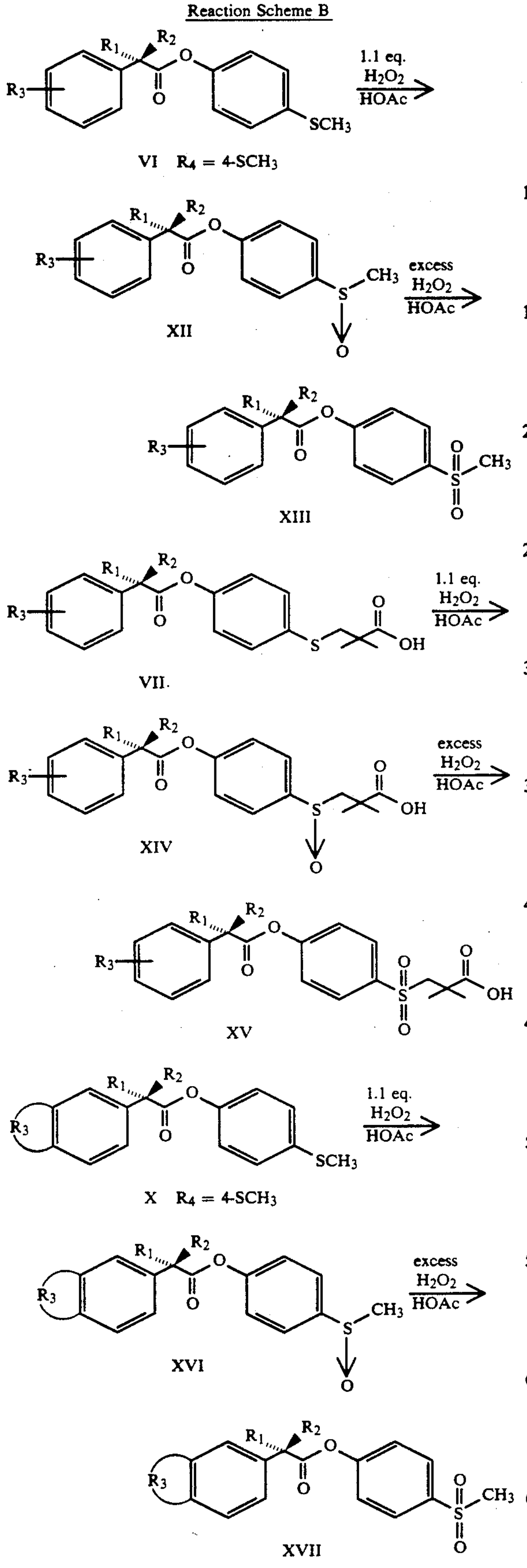
VI $R_4$ = 4-$SCH_3$
XII
XIII
VII.
XIV
XV
X $R_4$ = 4-$SCH_3$
XVI
XVII
-continued
Reaction Scheme B
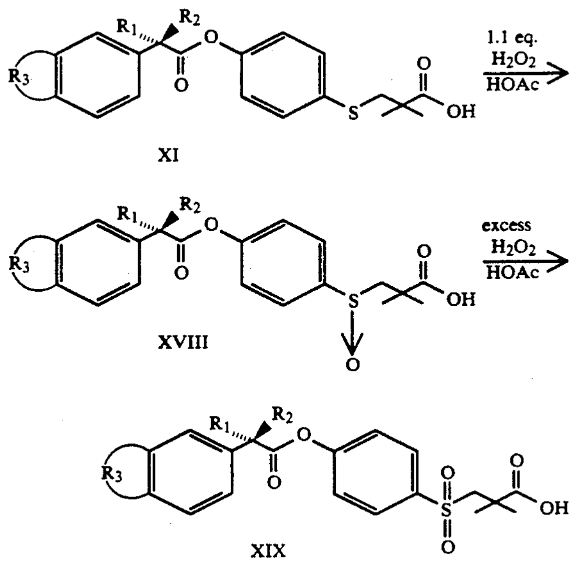
XI
XVIII
XIX
Reaction Scheme C
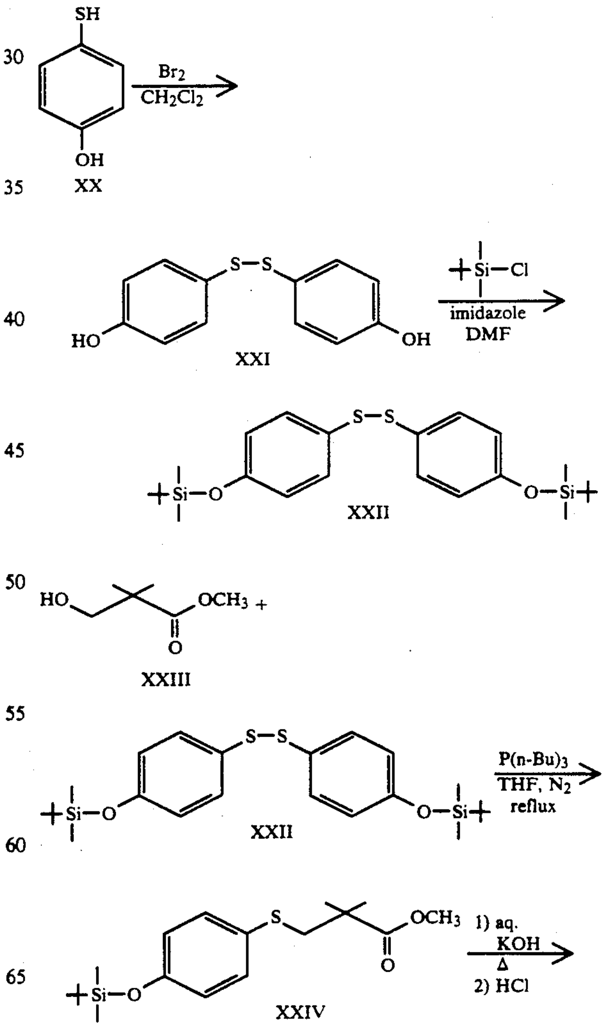
XX
XXI
XXII
XXIII
XXII
XXIV -continued
Reaction Scheme C
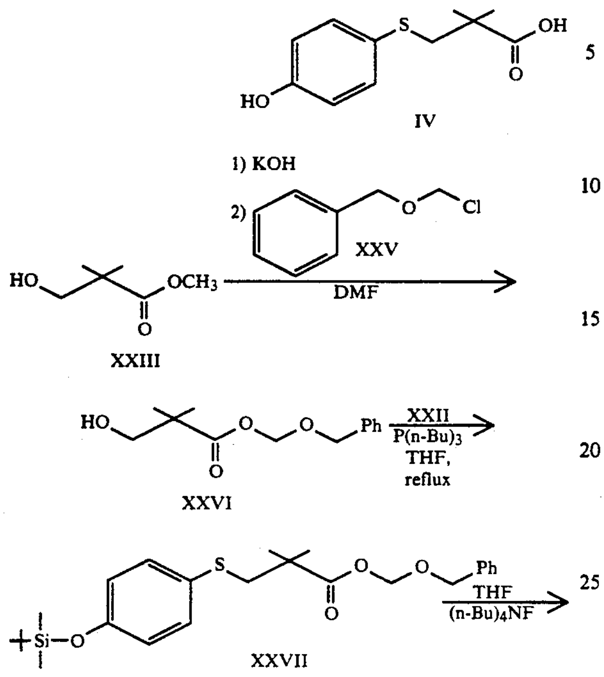
-continued
Reaction Scheme C
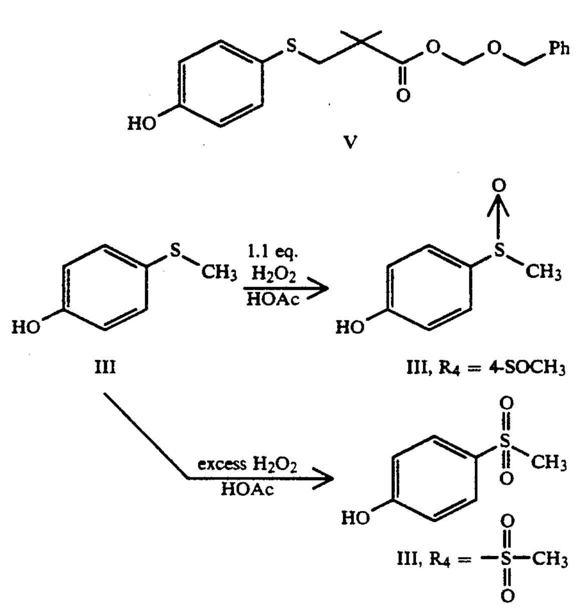
Reaction Scheme D
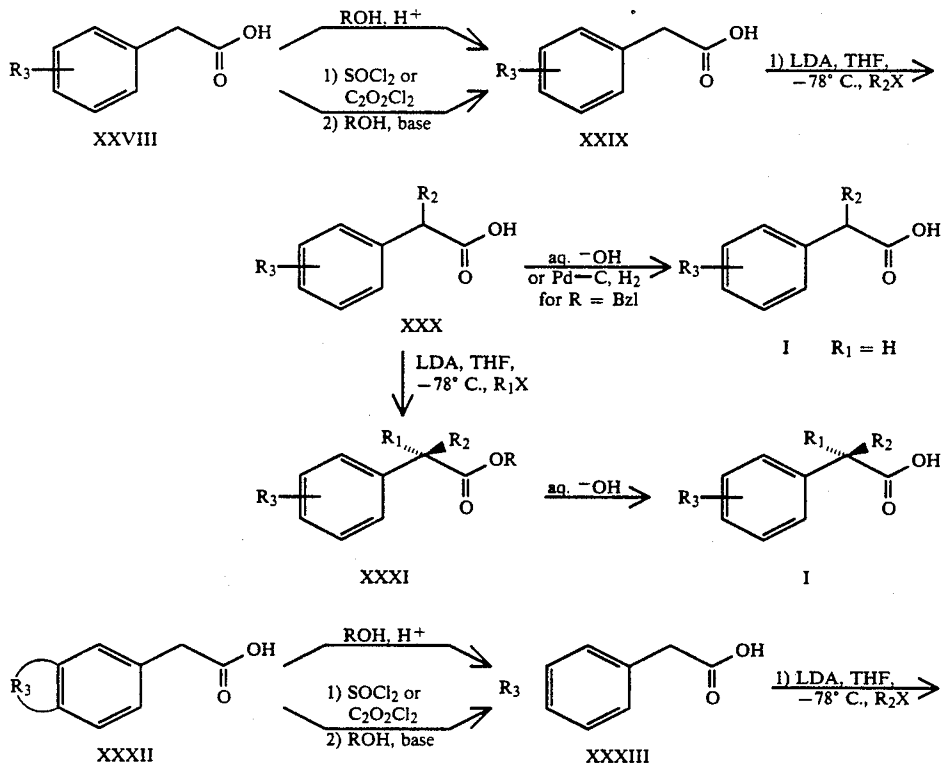

-continued
Reaction Scheme D
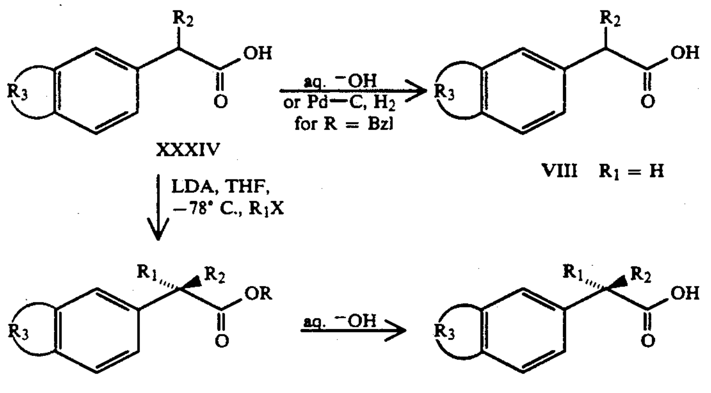
XXXV VIII
Reaction Scheme E
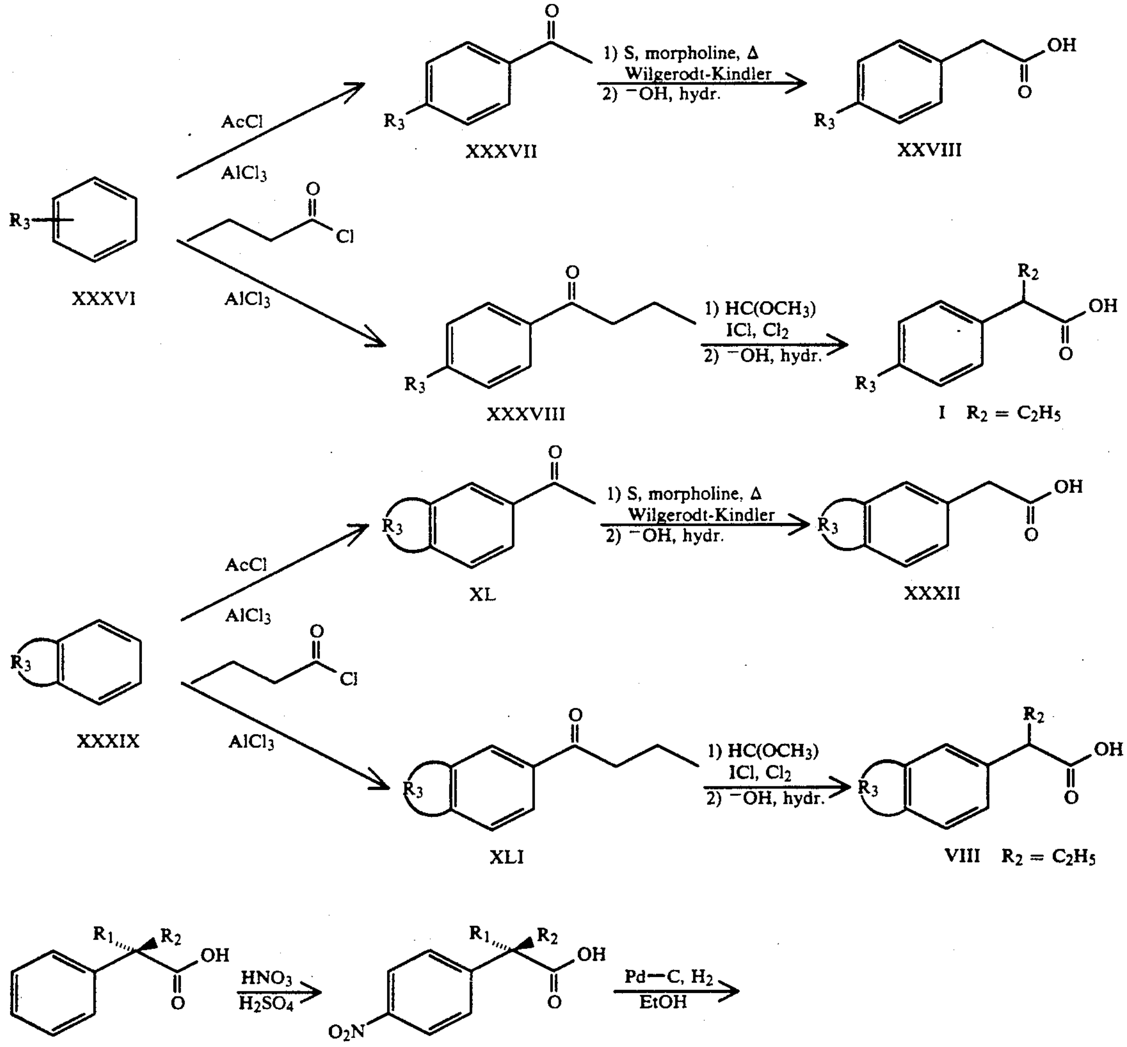
I
$R_3 = H$
I
$R_3 = 4\text{-}NO_2$ -continued Reaction Scheme E

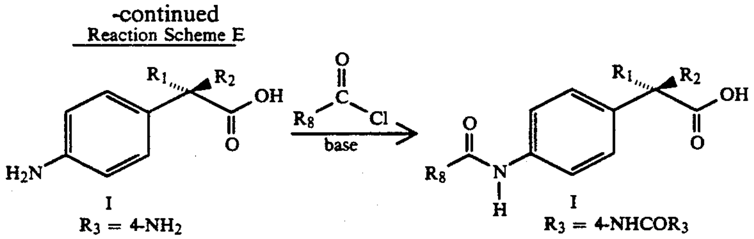

I, $R_3$ = 4-$NH_2$ → I, $R_3$ = 4-$NHCOR_3$

As depicted in Reaction Scheme A, the aromatic esters (VI, VII, X and XI) may be obtained by reaction of the appropriate acid chloride (II, IX) derived from the substituted phenylalkanoic acids I and VIII respectively and the desired phenol derivative (III, IV, or V) in the presence of organic bases such as triethylamine, pyridine or other commonly used reagents. Alternately, a solution of the acid (I or VIII) and the phenol component (III or V) may be treated with any of the carbodiimides (dicyclohexylcarbodiimide [DCC] for example) already in use in the field of synthetic organic chemistry to afford the corresponding aromatic esters (VI, X). In the instances where the phenolic ester (V) is utilized above, the benzyloxymethylene (BOM) protecting group is removed subsequent to the coupling reaction to afford the free carboxylic acid derivatives (VII, XI). The BOM groups which may be utilized to prevent undesirable side reactions between the carboxylic acid moiety of the phenol (IV) and the acid chlorides (II, IX) or the nascent symmetrical anhydrides present during the coupling reactions.

It will be evident to those skilled in the art that each of the aforementioned reactions may require slightly different conditions, dependent on the reactants involved, to obtain the best yields of the desired products. In certain cases, for example, the substituent $R_3$ may be incompatible with some of the reagents utilized in the overall reaction pathway. In those instances, an appropriate protecting group must be chosen for $R_3$ to prevent undesired side reactions. For example, if $R_3$ is hydroxy, protection as the t-butyldimethylsilyl ether or benzyl ether will allow the reaction sequence to proceed as specified. The conditions for introducing and removing protecting groups, whether or not such protecting groups are needed, are known to anyone skilled in the art.

In cases where the phenol components bear a substituent containing a sulfur atom directly attached to the aromatic ring (IV, V, III with $R_4$=$SCH_3$), the corresponding esters (VI, VII, X, XI) may be oxidized to the respective sulfoxides (XII, XIV, XVI, XVIII) by treatment with one equivalent of hydrogen peroxide or to the sulfones (XIII, XV, XVII, XIX) by oxidation with excess peroxide as described in Reaction Scheme B. The sulfones (XIII, XV, XVII, XIX) are obtained directly from the sulfides (VI, VII, X, XI) without isolation of the intermediate sulfoxides formed initially in the presence of excess peroxide.

The phenolic compounds (III) are available commercially. The other derivatives (IV, V) may be synthesized from readily available starting materials as described in Reaction Scheme C. 4-Hydroxythiophenol (XX) may be oxidized to the disulfide (XXI) in high yield. Subsequent masking of the hydroxyls of (XXI) with suitable protecting groups (tert-butyldimethylsilyl, for example) may be effected by treatment of the disulfide (XXI) with two equivalents of tert-butyldimethylsilylchloride in the presence of imidazole in DMF. There are numerous examples of protecting groups for phenolic moieties published in the general synthetic chemistry literature (see Greene, T. W., "Protective Groups in Organic Synthesis", John Wiley and Sons, 1981). It is contemplated that other available protecting groups could function similarly to the tert-butyldimethylsilyl example cited above. These additional protecting groups as well as the reaction conditions for incorporating these groups at the appropriate point in the synthesis are well known to practitioners skilled in the art.

Reaction of the protected disulfide (XXII) with tri-n-butylphosphine in the presence of the appropriate alcohol (XXIII or XXVI) provides the thioethers (XXIV and XXVII respectively). Hydrolysis of the ester (XXIV) in aqueous KOH results in cleavage of the silyl ether as well to give the phenolic acid (IV). The BOM protected derivative (XXVII) may be selectively desilylated with tetra-n-butylammonium fluoride in aqueous THF to yield the BOM protected phenol (V). The commercially available 4-methylmercaptophenol (III, $R_4$=4-$SCH_3$) may be converted to the sulfoxide (III, $R_4$=4—$S(O)CH_3$) and the sulfone (III, $R_4$=4—$S(O)_2CH_3$) by oxidation with hydrogen peroxide in acetic acid under the conditions specified in Reaction Scheme C.

As illustrated in Reaction Scheme D, the appropriate phenylacetic acids (XXVIII, XXXII) whether or not additionally substituted by substituent $R_3$ may be esterified by treatment with thionyl chloride ($SOCl_2$), or oxalyl chloride ($C_2O_2Cl_2$) to generate the acid chloride which is subsequently allowed to react with the appropriate alcohol (ROH) in the presence of base or alternately by acid catalyzed esterification.

The phenylacetic acid esters (XXIX, XXXIII) thus obtained may be alkylated at the α-position by generation of the enolate anion with strong bases such as lithium diisopropylamide (LDA) followed by reaction of the enolate with the appropriate alkyl halide. The resulting 2-phenylalkanoates (XXX, XXXIV) may be converted to the corresponding 2-phenylalkanoic acid derivatives (I, VIII) by base hydrolysis of the alkyl esters and hydrogenolysis of the benzyl esters.

The alkylated esters (XXX, XXXIV) may be alkylated further to yield the α,α-dialkyl esters (XXXI, XXXV). Hydrolysis of the esters (XXXI, XXXV) affords the dialkylated acids (I, VIII). If $R_2X$=$Br(CH_2)_nBr$ then the corresponding esters (XXX, XXXIV) have $Br(CH_2)_n$— as the $R_2$ substituent and subsequent treatment with LDA results in formation of the 1-phenylcycloalkane carboxylates (XXXI, XXXV, $R_1$, $R_2$=—$(CH_2)_n$—) which may be saponified to the corresponding 1-phenylcycloalkane carboxylic acids (I, VIII, $R_1$, $R_2$=—$(CH_2)_n$—).

A number of substituted phenylacetic acids and 2-phenylalkanoic acids are commercially available and may be obtained directly for use herein. Acids (I) and (VIII) bearing substituents $R_3$ which are not available may be synthesized by published procedures. Reaction Scheme E describes some of the many examples of these types of procedures which are known to those skilled in the art.

Benzene derivatives (XXXVI, XXXIX) may be acylated by the Friedel Crafts procedure to give arylketones. The substituted acetophenones (XXXVII, XL) may be transformed to the phenylacetic acids (XXVIII, XXXII) by the Wilgerodt-Kindler reaction sequence. The butyrophenone derivatives (XXXVIII, XLI) may be oxidatively rearranged to the phenylbutyric acids (I, VIII, $[R_2=C_2H_5]$) by commonly used techniques. Additionally, available phenylalkanoic acids (I) may be nitrated to provide the 4-nitro derivative (I, $R_3$=4—$NO_2$). Reduction of the nitro substituent gives the amino compound (I, $R_3$=4—$NH_2$) which may be acylated to afford the amides (I, $R_3$=4—$NHCOR_8$).

It will be evident to one skilled in this field of chemistry that there are additional generally available methods of synthesizing the compounds of the invention.

The following examples are given to illustrate the preparation of specific compounds according to the invention:

EXAMPLE 1

Synthesis of 4-Nitrophenyl 2-(4'-Methoxyphenyl)butyrate (34)

Oxalyl chloride (12 mL of a 2.0M solution in $CH_2Cl_2$) was added under nitrogen to a solution of 2-(4'-methoxyphenyl)butyric acid (4.66 g, 24 mmol) in 25 mL of $CH_2Cl_2$ and stirred at room temperature overnight. The volatiles were removed under vacuum and the residue was distilled to afford 4.46 g (87%) of pure 2-(4'-methoxyphenyl)butyryl chloride. $^1H$ NMR ($CDCl_3$) δ0.919 (t, 3H, J=7.4 Hz), 1.78–1.92 (m, 1H), 2.13–2.27 (m, 1H), 3.81 (s, 3H), 3.83 (t, 1H, J=7.6 Hz), 6.91 (d, 2H, J=8.8 Hz), 7.21 (d, 2H, J=8.7 Hz); $^{13}C$ NMR ($CDCl_3$) δ11.43, 26.26, 55.14, 64.21, 114.50, 127.86, 129.65, 159.75, 175.48.

The acid chloride (1.06 g, 5.0 mmol) was added to a mixture of 4-nitrophenol (0.696 g, 5.0 mmol) and pyridine (0.395 g, 5 mmol) in 5 mL of THF under $N_2$ and stirred overnight at room temperature. The solution was filtered and concentrated under vacuum to give a yellow residue which was chromatographed on a flash silica gel column ($CH_2Cl_2$) to afford 1.46 g (92%) of the desired nitrophenyl ester. $^1H$ NMR ($CDCl_3$) δ0.988 (t, 3H, J=7.3 Hz), 1.83–1.97 (m, 1H), 2.13–2.28 (m, 1H), 3.67 (t, 1H, J=7.7 Hz), 3.82 (s, 3H), 6.92 (d, 2H, J=8.4 Hz), 7.18 (d, 2H, J=9.3 Hz), 7.31 (d, 2H, J=8.4 Hz), 8.23 (d, 2H, J=9.2 Hz).

EXAMPLE 2

Synthesis of 4-Methylmercaptophenyl 2-(4'-Methoxyphenyl)butyrate (35)

To a stirred solution of 4-methylmercaptophenol (0.701 g, 5.0 mmol) and pyridine (0.395 g, 5.0 mmol) in 5 mL of THF under $N_2$ was added a solution of 2-(4'-methoxyphenyl)butyryl chloride (1.06 g, 5.0 mmol) in 5 mL of THF. After stirring at room temperature overnight, the precipitated pyridinium hydrochloride was filtered off and the filtrate evaporated to give 1.76 g of crude ester. Kugelrohr distillation afforded 1.53 g of the pure ester (95% yield). $^1H$ NMR ($CDCl_3$) δ0.974 (t, 3H, J=7.4 Hz), 1.80–1.93 (m, 1H), 2.13–2.25 (m, 1H), 2.45 (s, 3H), 3.63 (t, 1H, J=7.7 Hz), 3.81 (s, 3H), 6.90 (d, 2H, J=8.7 Hz), 6.92 (d, 2H, J=8.6 Hz), 7.23 (d, 2H, J=8.7 Hz), 7.31 (d, 2H, J=8.7 Hz); $^{13}C$ NMR ($CDCl_3$) δ11.84, 16.25, 26.49, 52.46, 55.13, 114.19, 122.06, 128.09, 129.17, 130.69, 135.68, 148.77, 159.15, 173.15.

EXAMPLE 3

Synthesis of 4-Methylsulfinylphenyl 2-(4'-Methoxyphenyl)butyrate (36)

4-Methylmercaptophenyl 2-(4'-methoxyphenyl) butyrate (6.0 g, 19 mmol) in 63 g of glacial acetic acid was treated with 3.2 mL of 30% $H_2O_2$. The reaction was followed by TLC (silica, $CH_2Cl_2$) until all of the starting material was consumed. The product sulfoxide was extracted into ether. The ether layer was washed with $H_2O$ followed by saturated sodium bicarbonate and then dried over anhydrous potassium carbonate for 16 hours. The solution was filtered and evaporated under vacuum to give the pure product (5.2 g, 82%). $^1H$ NMR ($CDCl_3$) δ0.981 (t, 3H), 1.80–1.95 (m, 1H), 2.12–2.28 (m, 1H), 2.69 (s, 3H), 3.66 (t, 1H), 3.80 (s, 3H), 6.91 (d, 2H), 7.16 (d, 2H), 7.31 (d, 2H), 7.63 (d, 2H); $^{13}C$ NMR ($CDCl_3$) δ11.78, 26.33, 43.91, 52.39, 55.10, 114.24, 122.75, 124.93, 129.12, 130.25, 142.88, 153.06, 159.22, 172.75.

EXAMPLE 4

Synthesis of 4-Methylsulfonylphenyl 2-(4'-Methoxyphenyl)butyrate (37)

4-Methylmercaptophenyl 2-(4'-methoxyphenyl) butyrate (10.0 g, 31.6 mmol) was dissolved in 32 mL of glacial acetic acid, 30% $H_2O_2$ (32 mL) was added and the solution stirred for 72 hours. The reaction mixture was poured into 250 mL of ice water and stirred for 30 minutes until all of the ice had melted. The white solid was filtered off and washed with water until the filtrate was neutral. The product was dried under vacuum to give 10.5 g (95%) of the desired compound. $^1H$ NMR ($CDCl_3$) δ0.986 (t, 3H, J=7.5 Hz), 1.83–1.96 (m, 1H), 2.13–2.27 (m, 1H), 3.04 (s, 3H), 3.67 (t, 1H, J=7.7 Hz), 3.82 (s, 3H), 6.92 (d, 2H, J=8.7 Hz), 7.21 (d, 2H, J=8.7 Hz), 7.31 (d, 2H, J=8.7 Hz), 7.94 (d, 2H, J=8.7 Hz); $^{13}C$ NMR ($CDCl_3$) δ12.10, 26.61, 44.78, 52.76, 55.47, 114.66, 123.05, 129.47, 129.58, 130.35, 138.17, 155.45, 159.65, 172.79.

EXAMPLE 5

Synthesis of 2,2-Dimethyl-3-(4'-Hydroxyphenylthio)propionic acid (IV)

A) A solution of bromine (95 g, 0.59 mol) in 500 mL of $CH_2Cl_2$ was added dropwise to a solution of 4-hydroxythiophenol (150 g, 1.19 mol) in 500 mL of $CH_2Cl_2$ until the orange color persisted. The reaction mixture was stirred overnight, 1 L of petroleum ether was added and the solid was filtered and dried under vacuum to give 98.5 g (67%) of 4'-hydroxyphenyldisulfide.

B) 4'-Tert-butyldimethylsilyloxyphenyldisulfide (XXII).

Solid t-butyldimethylsilylchloride (132.6 g, 0.88 mol) was added to a stirred solution of 4'-hydroxyphenyldisulfide (100.1 g, 0.40 mol) and imidazole (119.8 g, 1.76 mol) in 500 mL of DMF under nitrogen. After 2 hours the reaction mixture was poured into 750 mL of $H_2O$ and extracted with ether (3×300 mL). The combined ether layers were washed with $H_2O$, dried over $MgSO_4$ and evaporated to give 201.0 g of the product as a yellow liquid. The crude product can be purified further by vacuum distillation or chromatography on silica gel (pet. ether) to give the desired compound in a near quantitative yield.

C) Methyl 2,2-dimethyl-3-(4'-tert-butyldimethylsilyloxyphenylthio)propionate (XXIV).

Methyl 2,2-dimethyl-3-hydroxypropionate (4.23 g, 32 mmol), 4'-tert-butyldimethylsilyloxyphenyldisulfide (14.36 g, 30 mmol) and tri-n-butylphosphine (6.06 g, 30 mmol) were heated together under reflux for 48 hours under a nitrogen atmosphere. The reaction mixture was concentrated under vacuum, $H_2O$ was added and the mixture extracted with pet. ether. After drying over $MgSO_4$, the solution was concentrated to give 20.72 g of a clear liquid. The product was isolated by chromatography on silica gel. The by-product 4-tert-butyldimethylsilyloxythiophenol (7.35 g, 102%) eluted first with pet. ether. The thioether product (7.98 g, 75%) was eluted with 50:50 pet. ether/$CH_2Cl_2$. $^1H$ NMR ($CDCl_3$) δ 0.175 (s, 6H), 0.965 (s, 9H), 1.25 (s, 6H), 3.08 (s, 2H), 3.55 (s, 3H), 6.75 (d, 2H, J=8.4 Hz), 7.29 (d, 2H, J=8.4 Hz); $^{13}C$ NMR ($CDCl_3$) δ−4.81, 17.91, 24.55, 25.39, 43.81, 46.52, 51.62, 120.72, 128.21, 133.36, 155.18, 176.98.

D) 2,2-Dimethyl-3-(4'-hydroxyphenylthio)-propionic acid (IV).

Methyl 2,2-dimethyl-3-(4'-tert-butyldimethylsilyloxyphenylthio)propionate (7.09 g, 20 mmol) was added to KOH (6.73 g, 120 mmol) in 40 mL of $H_2O$ and the mixture was heated to reflux overnight. The reaction mixture was cooled to room temperature, diluted with 40 mL of $H_2O$ and extracted with ether. The aqueous layer was separated, acidified to pH=2 and extracted with ether (3×100 mL). The combined ether layers were dried over anhydrous $MgSO_4$, filtered and evaporated to give 3.72 g (82%) of 2,2-dimethyl-3-(4'-hydroxyphenylthio)propionic acid as a white solid. $^1H$ NMR ($CD_3COCD_3$) δ1.25 (s, 6H), 3.11 (s, 2H), 6.80 (d, 2H, J=8.4 Hz), 7.31 (d, 2H, J=8.7 Hz), 8.6 (br s, 1H, —OH); $^{13}C$ NMR ($CD_3COCD_3$) δ25.13, 44.53, 47.63, 117.21, 127.46, 134.67, 158.18, 178.41.

EXAMPLE 6

Synthesis of 4-(2'-Carboxy-2'-methylpropylmercapto)phenyl 2-Phenylbutyrate (323)

A) 2-Phenylbutyryl chloride

Thionyl chloride (0.12 mol) in 60 mL of $CH_2Cl_2$ was added to a stirred solution of 2-phenylbutyric acid (16.4 g, 0.10 mol). A catalytic amount of DMF was added and the reaction was allowed to continue overnight at room temperature. The volatiles were removed under vacuum and the residual liquid was vacuum distilled to yield 12.4 g (68%) of 2-phenylbutyryl chloride. IR (neat) 1798 $cm^{-1}$ (C=O).

B) 4-(2'-Carboxy-2'-methylpropylmercapto)-phenyl 2-phenylbutyrate.

A solution of 2-phenylbutyryl chloride (1.19 g, 6.5 mmol) in 5 mL of THF was added to a stirred solution of 2,2-dimethyl-3-(4'-hydroxyphenylthio)-propionic acid (1.36 g, 6.0 mmol) and pyridine (1.03 g, 13.0 mmol) in 10 mL of THF under $N_2$. After 6 days, 30 mL of ether was added and the reaction mixture filtered into a separatory funnel. The organic layer was washed with 0.5N HCl (2×15 mL), saturated NaCl (15 mL), 1:9 saturated $NaHCO_3/H_2O$ (2×15 mL), saturated NaCl (15 mL) and dried over anhydrous $MgSO_4$. Filtration and evaporation provided 1.96 g (88%) of the desired ester. $^1H$ NMR ($CDCl_3$) δ0.974 (t, 3H, J=7.2 Hz), 1.27 (s, 6H), 1.82–1.96 (m, 1H), 2.13–2.28 (m, 1H), 3.13 (s, 2H), 3.67 (t, 1H, J=7.5 Hz), 6.90 (d, 2H, J=8.7 Hz), 7.30–7.38 (ArH, 7H), 11.9 (br s, —OH); $^{13}C$ NMR ($CDCl_3$) δ11.84, 24.30, 26.45, 43.73, 44.95, 53.27, 122.06, 127.58, 128.01, 128.88, 131.66, 134.27, 138.58, 149.65, 172.75, 183.22.

EXAMPLE 7

Synthesis of 4-(2'-Carboxy-2'-methylpropylsulfinyl)phenyl 2-Phenylbutyrate (324)

To a solution of 4-(2'-carboxy-2'-methylpropylmercapto)phenyl 2-phenylbutyrate (745 mg, 2 mmol) in 1 mL of glacial acetic acid was added 0.25 mL of 30% $H_2O_2$. Additional 0.25 mL aliquots of 30% $H_2O_2$ were added at one-half hour intervals until TLC indicated complete consumption of the starting material. The reaction was quenched with 20 mL of $H_2O$, extracted with $Et_2O$ (2×25 mL), dried over anhydrous $MgSO_4$ and evaporated to give the sulfoxide containing a residual amount of acetic acid. The residue was suspended in 20 mL of $H_2O$, the mixture was shell frozen and lyophilized to give 506 mg (65%) of the pure product sulfoxide. $^1H$ NMR ($CDCl_3$) δ1.00 (t, 3H, J=7.4 Hz), 1.42 (s, 3H), 1.54 (s, 3H), 1.85–1.99 (m, 1H), 2.16–2.31 (m, 1H), 3.07 (s, 2H), 3.72 (t, 1H, J=7.6 Hz), 7.17 (d, 2H, J=8.7 Hz), 7.32–7.40 (ArH, 5H), 7.70 (d, 2H, J=8.7 Hz), 11.17 (br s, —OH); $^{13}C$ NMR ($CDCl_3$) δ 11.83, 24.54, 25.71, 26.39, 41.73, 53.26, 68.81, 122.75, 125.60, 127.73, 128.10, 128.98, 138.30, 141.34, 153.11, 172.49, 180.33.

EXAMPLE 8

Synthesis of 4-(2'-Carboxy-2'-methylpropylsulfonyl)phenyl 2-Phenylbutyrate (325)

To a stirred solution of 4-(2'-carboxy-2'-methylpropylmercapto)phenyl 2-phenylbutyrate (745 mg, 2 mmol) in 4 mL of glacial acetic acid was added 4 mL of 30% hydrogen peroxide. After 36 hours the reaction was quenched with 20 mL of $H_2O$, extracted with $Et_2O$ (2×25 mL), dried over anhydrous $MgSO_4$ and evaporated under vacuum. The residue was suspended in $H_2O$, shell frozen and lyophilized to afford 728 mg (90%) of pure 4-(2'-carboxy-2'-methylpropylsulfonyl)-phenyl 2-phenylbutyrate. $^1H$ NMR ($CDCl_3$) δ0.992 (t, 3H, J=7.4 Hz), 1.46 (s, 6H), 1.85–2.00 (m, 1H), 2.16–2.30 (m, 1H), 3.47 (s, 2H), 3.72 (t, 1H, J=7.6 Hz), 7.20 (d, 2H, J=8.7 Hz), 7.32–7.38 (ArH, 5H), 7.92 (d, 2H, J=8.7 Hz), 10.9 (br s, —OH); $^{13}C$ NMR ($CDCl_3$) δ11.79, 24.94, 26.33, 41.21, 53.26, 64.32, 122.63, 127.83, 128.08, 129.03, 129.64, 138.07, 138.33, 155.06, 172.18, 181.47.

EXAMPLE 9

Synthesis of Benzyloxymethyl 2,2-Dimethyl-3-(4'-Hydroxyphenylthio)propionate (V)

A) Benzyloxymethyl 2,2-dimethyl-3-hydroxypropionate (XXVI).

A solution of methyl 2,2-dimethyl-3-hydroxypropionate (25.0 g, 0.189 mol) in 100 mL of MeOH was treated with a solution of KOH (11.7 g, 0.208 mol) in 50 mL of $H_2O$ and the resulting mixture stirred at room temperature for 5 hours. The reaction mixture was heated under reflux for 30 minutes, methanol was distilled and the remaining solution shell frozen and lyophilized to give 26.7 g (90.6%) of potassium 2,2-dimethyl-3-hydroxypropionate as a white solid. The potassium salt (13.0 g, 0.083 mol) was suspended in 100 mL of dry DMF and chloromethylenebenzylether (14.3 g, 0.092 mol) was added. After stirring 48 hours at room temperature the mixture was quenched with 100 mL of $H_2O$ and extracted with $Et_2O$ (200 mL). The ether layer was separated, washed with $H_2O$ (3×100 mL), saturated NaCl (100 mL) and dried over $MgSO_4$. Evaporation and distillation of the residue gave 13.6 g (73%) of benzyloxymethyl 2,2-dimethyl-3-hydroxypropionate as a clear liquid.

B) Benzyloxymethyl 2,2-dimethyl-3-(4'-tert-butyldimethylsilyloxyphenylthio)propionate (XXVII).

Benzyloxymethyl 2,2-dimethyl-3-hydroxypropionate (2.40 g, 10.2 mmol), 4'-tert-butyldimethylsilyloxyphenyldisulfide (4.89 g, 10.2 mmol) and tri-n-butylphosphine (2.07 g, 10.2 mmol) were heated together under reflux in 30 mL of THF under a nitrogen atmosphere for 18 hours. The reaction mixture was diluted with ether, washed with $H_2O$ (3×100 mL), dried over anhydrous $MgSO_4$ and evaporated. The residue was chromatographed on silica gel (pet. ether/$CH_2Cl_2$) to give 1.82 g (39%) of the desired product. $^1H$ NMR ($CDCl_3$) δ0.181 (s, 6H), 0.975 (s, 9H), 1.28 (s, 6H), 3.12 (s, 2H), 4.67 (s, 2H), 5.28 (s, 2H), 6.75 (d, 2H, J=8.7 Hz), 7.2–7.4 (m, 7H); $^{13}C$ NMR ($CDCl_3$) δ−4.80, 17.91, 24.45, 25.39, 44.15, 46.25, 71.70, 88.63, 120.79, 127.87, 128.03, 128.09, 128.18, 128.59, 133.27, 137.16, 155.21, 176.07.

C) Benzyloxymethyl 2,2-dimethyl-3-(4'-hydroxyphenylthio)propionate (V).

A 1.0M solution of tetra-n-butylammonium fluoride in THF (3.6 mL, 1.1 equiv) was added to the tert-butyldimethylsilylether (XXVII) (1.50 g, 3.3 mmol) in 25 mL of THF at −10° C. After 1 hour the reaction was acidified with saturated ammonium chloride (25 mL) and extracted with ether. The ether layer was washed with $H_2O$, saturated NaCl, dried over anhydrous $MgSO_4$ and concentrated. The residue was chromatographed on silica gel to give 0.92 g (82%) of V. $^1H$ NMR ($CDCl_3$) δ1.27 (s, 6H), 3.10 (s, 2H), 4.67 (s, 2H), 5.10 (br s, 1H), 5.28 (s, 2H), 6.74 (d, 2H, J=8.4 Hz), 7.2–7.4 (m, 7H); $^{13}C$ NMR ($CDCl_3$) δ25.10, 44.82, 47.19, 72.41, 89.38, 116.72, 128.07, 128.68, 128.76, 129.24, 134.49, 137.74, 155.91, 176.91.

EXAMPLE 10

Synthesis of 4-(2'-Carboxy-2'-methylpropylmercapto)phenyl 2-(4'-Methoxyphenyl)isobutyrate (308)

A solution of 2-(4'-methoxyphenyl)isobutyric acid (1.5 g, 7.7 mmol) in $CH_2Cl_2$ was treated with a 2.0M oxalyl chloride solution in $CH_2Cl_2$ (7.7 mL, 15.4 mmol) and a drop of DMF. After stirring overnight at room temperature, the volatiles were removed under vacuum and the residue dissolved in dry THF. The resulting solution of 2-(4'-methoxyphenyl)isobutyryl chloride was added to a stirred solution of V (2.68 g, 7.7 mmol) and pyridine (0.73 g, 9.3 mmol) in THF and stirred overnight. The reaction mixture was concentrated under vacuum, the residue dissolved in ether and washed with $H_2O$. The organic layer was washed subsequently with dilute HCl, dilute bicarbonate, $H_2O$ and dried over anhydrous $MgSO_4$. The product was isolated by preparative HPLC to afford 1.1 g (27%) of the benzyloxymethyl protected ester. The benzyloxymethyl group was removed by treatment with 40 mL of 6N HCl/40 mL of THF for 1 hour. Saturated NaCl was added, the reaction mixture extracted with ether, washed with dilute bicarbonate solution, dried over anhydrous $MgSO_4$ and evaporated to give 0.75 g (89%) of 4-(2'-carboxy-2'-methylpropylmercapto)phenyl 2-(4'-methoxyphenyl)isobutyrate. $^1H$ NMR ($CDCl_3$) δ1.27 (s, 6H), 1.68 (s, 6H), 3.14 (s, 2H), 3.81 (s, 3H), 6.86–6.93 (m, 4H, ArH), 7.35–7.38 (m, 4H, ArH); $^{13}C$ NMR ($CDCl_3$) δ24.36, 26.22, 43.75, 45.08, 45.91, 55.16, 114.00, 122.04, 126.93, 131.85, 134.10, 136.18, 150.02, 158.69, 175.79, 182.77.

EXAMPLE 11

Synthesis of 4-(2'-Carboxy-2'-methylpropylmercapto)phenyl 2-(1',2',3',4'-Tetrahydro-6'-naphthyl)butyrate (389)

A solution of 2-(1',2',3',4'-tetrahydro-6'-naphthyl)butyryl chloride (4.0 mmol) in 16 mL of dry THF was added to a solution of IV (814 mg, 3.6 mmol) and pyridine (790 mg, 10 mmol) in 20 mL of dry THF and stirred under $N_2$ for 3 days. The THF was removed at the rotary evaporator and the residue dissolved in ether. The ether layer was washed successively with $H_2O$ (100 mL), dilute HCl, dilute $NaHCO_3$, dried over $MgSO_4$ and concentrated to give 1.35 g (79%) of the desired ester. $^1H$ NMR ($CDCl_3$) δ0.955 (t, 3H), 1.28 (s, 6H), 1.75–1.98 (m, s, 4H), 2.10–2.31 (m, 1H), 2.78 (br s, 4H), 3.14 (s, 2H), 3.59 (t, 1H), 6.92 (d, 2H), 7.01–7.19 (m, 3H, ArH), 7.37 (d, 2H), (—OH not observed); $^{13}C$ NMR ($CDCl_3$) δ11.96, 22.91, 23.95, 24.32, 26.59, 28.85, 29.21, 43.74, 45.04, 52.98, 122.16, 125.06, 128.75, 129.63, 131.74, 134.13, 135.63, 136.51, 137.66, 149.81, 173.00, 182.98.

EXAMPLE 12

Synthesis of 4-(Methylmercapto)phenyl 2-Phenylbutyrate (5)

To a flask containing 2-phenylbutyric acid (4.93 g, 30 mmol) in 40 mL of $CH_2Cl_2$ at 0° C. was added dicyclohexylcarbodiimide (6.19 g, 30 mmol) in 30 mL of $CH_2Cl_2$. Solid 4-methylmercaptophenol (4.21 g, 30 mmol) was added and the suspension stirred at room temperature overnight. The precipitated urea was filtered, the filtrate evaporated and the residue chromatographed on silica gel ($CH_2Cl_2$)to give 4-(methylmercapto)phenyl 2-phenylbutyrate (6.23 g, 73%) as a light yellow oil which was crystallized from EtOH to give white crystals (mp 28.0°–28.5° C.). $^1H$ NMR ($CDCl_3$) δ0.98 (t, 3H, J=7.3 Hz), 1.89 (m, 1H), 2.22 (m, 1H), 3.68 (t, 1H, J=7.6 Hz), 6.92 (d, 2H, J=8.6 Hz), 7.22 (d, 2H, J=8.6 Hz), 7.30–7.45 (m, 5H, ArH).

EXAMPLE 13

Synthesis of 4-(2'-Carboxy-2'-methylpropylmercapto)phenyl 2-(4'-Benzamidophenyl)butyrate (338)

A) 2-(4'-Nitrophenyl)butyric acid

A mixture of concentrated nitric acid (32 mL) and concentrated sulfuric acid (32 mL) were cooled in an ice salt bath. Solid 2-phenylbutyric acid (16.42 g, 100 mmol) was added in small portions maintaining the solution temperature below 10° C. The reaction was warmed to room temperature and allowed to stir for 1 hour. The product was isolated by pouring the reaction mixture onto 150 mL of crushed ice, filtering the white solid and recrystallizing from EtOH to give 14.5 g (69%) of the product as white crystals.

B) 2-(4'-Aminophenyl)butyric acid

A solution of 2-(4'-nitrophenyl)butyric acid (6.99 g, 33.4 mmol) in 250 mL of EtOH and 0.5 g of 10% Pd-C was hydrogenated overnight at 55 psi. The solution was filtered and evaporated under vacuum to give 5.50 g (92%) of the desired product.

C) 2-(4'-Benzamidophenyl)butyric acid

Benzoylchloride (7.84 g, 0.057 mol) was added dropwise to a solution of 2-(4'-aminophenyl)butyric acid (10.0 g, 0.057 mol) and pyridine (4.85 g, 0.061 mol) in 100 mL of THF at 0° C. After 30 minutes the ice bath was removed and the reaction warmed to room temperature. After 1 hour the suspension was diluted with 300 mL of ether, washed with 10% HCl (3×50 mL), saturated NaCl (50 mL), dried over $MgSO_4$ and evaporated to give a brown solid. Trituration with ether afforded 7.54 g (47.7%) of the product as a white solid.

D) 4-(2'-Carboxy-2'-methylpropylmercapto)phenyl 2-(4'-benzamidophenyl)butyrate

Dicyclohexylcarbodiimide (1.44 g, 7.0 mmol) was added to a solution of 2-(4'-benzamidophenyl)butyric acid (1.70 g, 6.0 mmol) and V (2.08 g, 6.0 mmol) in 60 mL of $CH_2Cl_2$ with stirring at room temperature. After 3 days, 4-dimethylaminopyridine (0.10 g) was added and the reaction was allowed to proceed an additional 24 hours. The reaction was quenched with 2 mL of acetic acid, filtered, washed with $H_2O$ (3×50 mL), saturated NaCl and dried over anhydrous $MgSO_4$. Removal of the solvent afforded 3.02 g (82%) of the product as a clear oil. The benzyloxymethyl group was removed by treating the oil (1.60 g, 2.6 mmol) with 50 mL of 6N HCl and 100 mL of THF at 0° C. for 1 hour followed by an additional 50 mL of THF and 50 mL of 6N HCL. After 1 hour the reaction was quenched with 50 mL of saturated NaCl and extracted with ether (300 mL). The ether layer was dried over $MgSO_4$, evaporated and the residue chromatographed to give the product as an oil which crystallized from EtOAc/hexane as a white solid (0.66 g, 52%). $^1H$ NMR ($CDCl_3$) δ0.983 (t, 3H, J=7.5 Hz), 1.29 (s, 6H), 1.8-2.3 (m, 2H), 3.14 (s, 2H), 3.67 (t, 1H, J=7.8 Hz), 6.91 (d, 2H, J=8.7 Hz), 7.37 (d, 2H, J=8.1 Hz), 7.45-7.6 (m, 5H, ArH), 7.64 (d, 2H, J=8.1 Hz), 7.87 (d, 2H, J=7.2 Hz), 7.97 (s, 1H), (—OH not observed); $^{13}C$ NMR ($CDCl_3$) δ11.87, 24.41, 26.44, 43.75, 45.10, 52.78, 120.66, 122.12, 127.22, 128.89, 129.01, 131.89, 132.15, 134.28, 134.72, 135.04, 137.45, 149.64, 166.17, 172.90, 182.17.

As noted earlier, the present compounds demonstrate HLE inhibiting activity which indicates that these compounds would be useful in the treatment of such diseases as emphysema, arthritis, atheriosclerosis or the like. For such uses, the compounds would be administered by the usual routes, e.g. orally, intravenously, subcutaneously, intraperitoneally or intramuscularly. For emphysema, the compounds would be administered in therapeutically effective amounts, usually orally or rectally, or as a mist for bronchial inhalation.

The amount of compound used to inhibit HLE will vary with the nature and extent of the condition involved. It is contemplated, for example, that mists containing from 0.05 to 20% of the active compound with dosages in the order of 2-100 mg per dosage unit several times a day would provide a therapeutically effective amount for the treatment of emphysema. Variations and adjustments in the size and frequency of administration can be determined to provide the desired HLE inhibition.

Pharmaceutical compositions containing the active compounds of the invention may comprise tablets, capsules, solutions or suspensions with conventional nontoxic pharmaceutically acceptable carriers. These compositions may include the usual types of additives, e.g. disintegrating or suspending agents or the like. Compounds selected for intravenous use should be soluble in aqueous solutions, while those used in, for example, oral formulations need not be water-soluble.

Topical formulations are also contemplated for use in the treatment of, for example, dermatitis and acne.

The compounds of the invention are extremely potent and highly selective inhibitors of neutrophil elastase. The compounds also appear to show adequate serum stability. The water solubility of the compounds varies and it will be appreciated that the ultimate mode of administration for each compound will depend, at least to some extent, on the solubility of the compound involved.

In this regard, it appears that water solubility of the present compounds may be improved, without undesirably affecting activity, selectivity or serum stability, by appropriate selection of the $R_4$ substituent(s) on the phenyl ring of the Formula (VI) compounds. These compounds may be viewed as made up of two components, i.e. an acylating group and a leaving group introduced by the acid and phenol reactants, respectively. The introduction of particular solubilizing substituents $R_4$ on the leaving group to improve solubility in aqueous solutions or buffers without undesirably affecting the activity of the compound is illustrated by the following data which compares a representative series of compounds with and without the modified leaving groups (TABLE III).

TABLE III

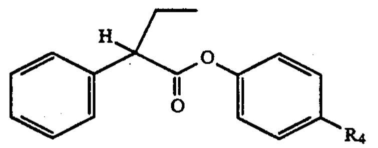

| $R_4$ | $I_{50}$ µm | PBS Solubility (mg/mL) |
|---|---|---|
| $-SCH_3$ | 9.000 | 0.010 |
| $-S(O)CH_3$ | 0.600 | 0.600 |
| $-S(O)_2CH_3$ | 0.100 | 0.010 |
| $-SCH_2C(CH_3)_2CO_2H$ | 0.892 | ≧2.00 |
| $-S(O)CH_2C(CH_3)_2CO_2H$ | 0.357 | ≧2.00 |
| $-S(O_2)CH_2C(CH_3)_2CO_2H$ | 0.141 | ≧2.00 |

Without intending to be limited to any theory of operation or function, it appears that the compounds of the invention bind to the active site of neutrophil elastase. More particularly, it appears that the acyl group binds to the S substrate position, i.e. the valine or proline-valine region of the binding pocket and the leaving group extends into the S' positions.

Representative compounds according to the invention have been compared with a compound (Compound A) typifying the compounds described in U.S. Pat. No. 4,801,610. The comparisons were directed towards potency (represented by the $I_{50}$'s for human neutrophil elastase (HNE), porcine pancreatic elastase (PPE) and alpha-chymotrypsin ($\alpha$-CH)), specificity (represented by the ratios of the $I_{50}$'s (PPE/HNE and $\alpha$-CH/HNE)) and the ability to inhibit the digestion of extracellular matrix by activated intact human neutrophils (expressed as a fraction of control) of the compounds listed. The following results were obtained (TABLE IV):

TABLE IV

| Compound | Structure | HNE $I_{50}$ | ECM (Fraction of Control 10 $\mu$M Inhibitor) | PPE ($I_{50}$) HNE ($I_{50}$) | $\alpha$-Chymotrypsin ($I_{50}$) HNE($I_{50}$) |
|---|---|---|---|---|---|
| Compound A | 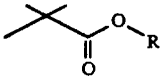 | 0.129 | 0.86 | 18.84 | 146.10 |
| 3 | 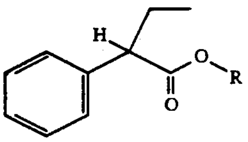 | 0.025 | 0.57 | 129.6 | 176.0 |
| 37 | 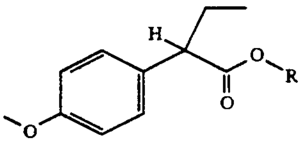 | 0.031 | 0.62 | 38.6 | 106.2 |
| 188 | 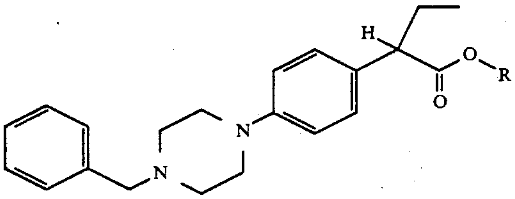 | 0.028 | 0.40 | 21.9 | 732.8 |
| 289 | 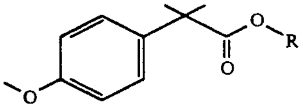 | 0.090 | 0.43 | 1294.0 | 1624.6 |
| 346 | 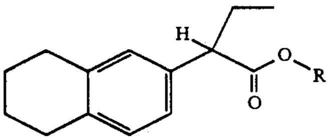 | 0.039 | 0.28 | 8.71 | 45.9 |
| 384 | 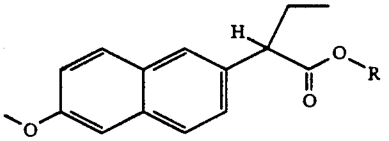 | 0.055 | 0.62 | 29.1 | 131.8 |

In all comparisons, R = 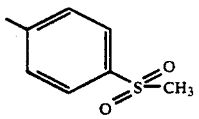

The above data indicate that the introduction of an aromatic ring substituent on the alpha carbon according to the invention will improve potency relative to a compound bearing a simple pivaloyl group (Compounds 3, 37, 188, 289, 346 and 384 versus Compound A). In addition, an aromatic substituent in place of a methyl group on the alpha carbon also significantly improves relative specificity, particularly with regard to porcine pancreatic elastase (PPE) (Compound 289 versus Compound A). Similarly, in the extracellular matrix (ECM) assay, which compares the ability of a compound to inhibit an intact neutrophil's digestion of extacellular matrix proteins, all of the herein disclosed compounds were more effective than the reference Compound A.

The following tests have been used to determine the activity of the compounds of the present invention:

Potency ($I_{50}$ Determination)

Reagents:

A) 0.075M sodium phosphate, 20% dimethyl sulfoxide (DMSO), pH 7.7=substrate and inhibitor buffer B) 0.075M sodium phosphate no DMSO, pH 7.7=inhibitor buffer C) 10 mM human neutrophil elastase (HNE) substrate =N-methoxysuccinyl-ala-ala-pro-val-pNA in DMSO D) 0.01M sodium acetate, 20% DMSO, pH 5.5=enzyme buffer (dilution)

E) 0.01M sodium acetate, pH 5.5=enzyme buffer (storage)

F) HNE (1 mg) dissolved in 1 mL of reagent E for storage at −20° C.

Make a 10 mM stock of the inhibitor in DMSO. Dilute an aliquot (10 μL) up to 1.0 mL in reagent A (100 μM). Serially dilute 100 μL of the 100 μM stock to 10.0, 1.0, 0.1, 0.01 μM in reagent A. Apply 100 μL of the diluted material to the wells of a 96-well plate. Dilute an aliquot of reagent F 1:150 in reagent D, apply 50 μL aliquots to the indicated wells and incubate for 7 minutes at room temperature.

The HNE substrate solution is made by taking 100 μL of reagent C into 500 μL of reagent A and 400 μL of reagent B. After the 7 minutes of incubation, the substrate (50 μL) is applied to each well. The HNE catalyzed reaction is then monitored spectrophotometrically at 405 nm using an ELISA plate reader machine (UVMAX, Molecular Devices) which processes the raw data with an on-board kinetics program. The enzyme activity is plotted against different inhibitor concentrations and the $I_{50}$ value is determined by using a curve fitting software program. Once the "screening" $I_{50}$ has been approximated, a more precise $I_{50}$ value can be obtained by examination of inhibitor concentrations around this value.

Specificity Determination

Reagents:

1) Porcine Pancreatic Elastase (PPE) 1 mg/mL in 0.01M sodium acetate, pH 5.5. An aliquot of this stock solution is diluted 1:20 in 0.01M sodium acetate, 20% DMSO, 10 mM $CaCl_2$, pH 5.5.

2) α-Chymotrypsin (α-CH) 1 mg/mL in 0.01M sodium acetate, pH 5.5. An aliquot of this stock solution is diluted 1:85 in 0.01M sodium acetate, 20% DMSO, 10 mM $CaCl_2$, pH 5.5, 0.005% triton X-100 detergent.

3) PPE substrate: N-succinyl-ala-ala-ala-pNA 20 mM stock in DMSO.

4) α-CH substrate: N-succinyl-ala-ala-pro-leu-pNA 20 mM stock in DMSO.

Inhibitor, substrate buffer: 0.1M tris-HCl, 0.01M $CaCl_2$, 0.005% triton X-100, 20% DMSO, pH 7.7.

Production of Extracellular Matrix (ECM)

1. Rat smooth muscle cells (R22), grown in a stock culture are detached from the flask surface with trypsin-/EDTA solution, washed with fetal calf serum-containing MEM and seeded at a concentration of 50,000 cells per well (1 mL/well) using a 24-well tissue culture plate.

2. Culture medium: Eagle's MEM with Earle's salts

1% penicillin/streptomycin

1% glutamine

10% heat inactivated fetal calf serum

2% tryptose phosphate broth

3. The cells are then grown to confluence (3–4 days), the medium removed and new medium containing $^3$H-proline (500 μCi/L) added.

4. At the same time the radioactive medium is added, 1 drop/well/day of an ascorbic acid solution (1.28 mg/mL of Hank's balanced salt solution) is added.

5. Fresh culture medium containing $^3$H-proline is added after 5 days and the culture continued for a total of 8–10 days.

6. The medium is then removed and the wells washed twice with phosphate buffered saline (PBS). The cells are lysed with 1 mL of 25 mM $NH_4OH$ for approximately 3–5 minutes, the solution is removed and the wells allowed to air dry (uncovered under UV light) overnight.

7. The wells are rinsed 3 times with PBS and frozen with 1 mL of PBS per well at −20° C.

8. When plates are required for the assay, they are thawed for 2 h at 37° C. and rinsed once with Hank's balanced salt solution.

Human Neutrophil Isolation and ECM Digestion Assay

1. Blood is drawn into heparinized syringes (1 mL/25 mL of blood).

2. Heparinized blood (25 mL) is then added to 15 mL of Hetastarch, gently mixed and the red cells allowed to settle for 25–30 minutes at room temperature.

3. The red cell free supernatant is then layered on top of a discontinous Percoll gradient (3 mL 74% Percoll; 3 mL 55%).

4. The tubes are then centrifuged at 1500×g for 20 minutes in a non-refrigerated centrifuge.

5. PMNs are then collected from the 74/55% interface, diluted and washed 2 times with saline.

6. If red cells are present, they are then lysed with deionized water for 15 seconds. Salt solution is added to return the salt concentration to 0.9% saline and the PMNs collected by centrifugation.

7. PMNs are then resuspended in Dulbecco's MEM containing 1% glutamine and 1% penicillin/streptomycin and counted using crystal violet dye.

8. The PMN concentration is then adjusted to $10^6$ cells/mL and aliquoted into the wells (1 mL/well) of the previously described $^3$H-proline ECM culture plate.

9. The cells are allowed to settle for 15 minutes and the inhibitor added, followed immediately by phorbol myristate acetate (PMA) (final concentration=10 nM).

10. The plates are then incubated at 37° C. and 100 μL aliquots of supernatant removed at various time points. The solubilized radioactivity is measured by liquid scintillation counting.

11. Radioactivity (counts/minute) from the background (no PMN) wells are then subtracted from the measured counts.

12. Inhibition is assessed by determining the ratio of counts found in the experimental wells (inhibitor added) to the counts obtained from the wells in which no inhibitor was added:

$$\text{fraction } ECM \text{ digestion} = \frac{(\text{counts from } PMA - \text{stimulated } PMN + \text{inhibitor}) - \text{blank}}{(\text{counts from } PMA - \text{stimulated } PMN \text{ alone}) - \text{blank}}$$

It will be appreciated that various modifications may be made in the invention described herein without departing from the spirit and scope of the invention as defined in the following claims wherein:

We claim:

1. A compound of the formula

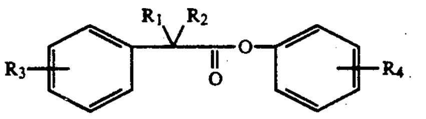

(VI)

wherein:

$R_1$ and $R_2$, which may be the same or different, are selected from the group consisting of hydrogen, alkyl of 1-6 carbons, cycloalkyl of 3-6 carbons or together represent a methylene group $-(CH_2)_n-$ where n is a whole number of from 1 to 6;

$R_3$ represents one or more substituents up to five selected from the group consisting of:

hydrogen, halogen, haloalkyl of 1-12 carbons, alkyl of 1-12 carbons, alkoxy of 1-12 carbons, alkenyl of 2-12 carbons, cycloalkyl of 3-12 carbons, mono- or dicyclic aryl, $-ZR_5$ where Z is O, S, S(O) or $SO_2$ and $R_5$ is hydrogen, alkyl of 1-18 carbons, cycloalkyl of 3-12 carbons or phenyl;

$-NR_6R_7$ where $R_6$ and $R_7$ may be the same or different and may be hydrogen, alkyl of 1-12 carbons, cycloalkyl or 3-6 carbons, phenyl, alkoxy of 1-12 carbons, acyl of the formula $-C(O)R_6$ is alkyl of 1-12 carbons, cycloalkyl of 3-12 carbons, phenyl, $CH_3OC(O)CH_2CH_2-$, $HOOCCH_2CH_2-$, $NaO_3SCH_2CH_2NHC(O)CH_2CH_2-$, or $R_6$ and $R_7$ together may represent $-C(O)CH_2CH_2C(O)-$, $-C(O)-C_6H_4-C(O)-$ or $-(CH_2)_x-$ where x is 2, 3, 4, 5 and 6;

morpholino, imidazole or piperazino joined to the phenyl ring through a nitrogen atom; or $R_3$ represents alkylene group containing 3 to 4 carbons, or such group substituted with lower alkoxy or the group $-O(CH_2)_nO-$ where n is 2, 3 or 4, joining adjacent carbons of the phenyl ring;

$R_4$ is from one to five substituents selected from hydrogen, halogen, nitro, $-C(O)CH_3$, $S(O)_pR_9$ where p is 1, 1 or 2 and $R_9$ is hydroxy, $-ONa$, or optionally substituted alkyl of 1-12 carbons or optionally substituted cycloalkyl, or the nontoxic, pharmaceutically acceptable salts thereof provided that $R_1$ and $R_4$ are not both hydrogen and provided further that $R_3$ is not haloalkyl when $R_4$ is hydrogen and $R_3$ is not alkyl when $R_4$ is nitro.

2. A compound according to claim 1 wherein one of $R_1$ and $R_2$ is hydrogen and the other is alkyl of 1-6 carbon atoms; $R_3$ is hydrogen, lower alkyl or cycloalkyl, lower alkoxy, phenyl, the atoms necessary to complete a ring with adjacent carbon atoms of the phenyl ring; $-NR_6R_7$ where $R_6$ is hydrogen and $R_7$ is $-C(O)R_8$ where $R_8$ is phenyl or $R_6$ and $R_7$ together represent $-(CH_2)_x-$ where x is 2-6.

3. A compound according to claim 2 wherein $R_4$ is $-S(O)_pR_9$ where p is 0, 1 or 2 and $R_9$ is optionally substituted alkyl of 1-12 carbons.

4. A compound according to claim 3 wherein $R_4$ is $-ZR_5$ where $R_5$ is a lower alkyl carboxylic acid group.

5. A compound according to claim 4 wherein $R_4$ is $-SCH_2C(CH_3)_2COOH$, $-S(O)CH_2C(CH_3)_2CO_2H$ or $-SO_2CH_2C(CH_3)CO_2H$.

6. A compound according to claim 1 wherein $R_4$ is $-SCH_3$ in the ortho or para position.

7. A compound according to claim 5 wherein $R_4$ is in the para position.

8. A compound according to claim 1 wherein $R_1$ and $R_2$ are different so as to be chiral.

9. A compound according to claim 1 wherein $R_1$ and $R_2$ are both methyl or ethyl or together form a cycloalkyl ring.

10. A pharmaceutical composition for inhibiting undesired elastase activity comprising an effective amount of a compound according to claim 1 and a carrier therefor.

11. A method of inhibiting elastase activity which comprises administering to a subject in need of such inhibition, an effective amount of a compound of the formula:

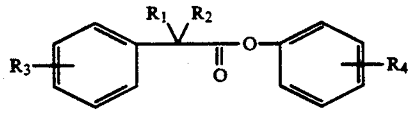

(VI)

wherein:

$R_1$ and $R_2$, which may be the same or different, are selected from the group consisting of hydrogen, alkyl of 1-6 carbons, cycloalkyl of 3-6 carbons or together represent a methylene group $-(CH_2)_n-$ where n is a whole number of from 1 to 6;

$R_3$ represents one or more substituents up to five selected from the group consisting of:

hydrogen, halogen, haloalkyl of 1-12 carbons, alkyl of 1-12 carbons, alkoxy of 1-12 carbons, alkenyl of 2-12 carbons, cycloalkyl of 3-12 carbons, mono- or dicyclic aryl, $-ZR_5$ where Z is O, S, S(O) or $SO_2$ and $R_5$ is hydrogen, alkyl of 1-18 carbons, cycloalkyl of 3-12 carbons or phenyl;

$-NR_6R_7$ where $R_6$ and $R_7$ may be the same or different and may be hydrogen, alkyl of 1-12 carbons, cycloalkyl or 3-6 carbons, phenyl, alkoxy of 1-12 carbons, acyl of the formula $-C(O)R_8$ is alkyl of 1-12 carbons, cycloalkyl of 3-12 carbons, phenyl, $CH_3OC(O)CH_2CH_2-$, $HOOCCH_2CH_2-$, $NaO_3SCH_2CH_2NHC(O)CH_2CH_2-$, or $R_6$ and $R_7$ together may represent $-C(O)CH_2CH_2C(O)-$, $-C(O)-C_6H_4-C(O)-$ or $-(CH_2)_x-$ where x is 2, 3, 4, 5 or 6;

morpholino, imidazole or piperazino joined to the phenyl ring through a nitrogen atom; or $R_1$ represents an alkylene group containing 3 to 4 carbons, or such group substituted with lower alkoxy or the group $-O(CH_2)_nO-$ where n is 2, 3 or 4, joining adjacent carbons or the phenyl ring;

$R_4$ is from one to five substituents selected from hydrogen, halogen, nitro, $-C(O)CH_3$, $S(O)_pR_9$ where p is 1, 1 or 2 and $R_9$ is hydroxy, $-ONa$, or optionally substituted alkyl of 1-12 carbons or optionally substituted cycloalkyl, or the nontoxic, pharmaceutically acceptable salts thereof provided that $R_3$ and $R_4$ are not both hydrogen and provided further that $R_3$ is not haloalkyl when $R_4$ is hydrogen and $R_3$ is not alkyl when $R_4$ is nitro.

12. A compound according to claim 1 wherein $R_1$ and $R_2$ are selected from the group consisting of hydrogen, alkyl of 1-6 carbons, cycloalkyl of 3-6 carbons or together represent a methylene group $-(CH_2)_n-$ where n is a whole number of from 1 to 6;

$R_3$ is alkyl in both the 3- and 4-positions or a polymethylene group joining the 3- and 4-positions; and $R_4$ is $-S(O)_pR_9$ where p is 0, 1 or 2 and $R_9$ is alkyl or carboxy-substituted alkyl of 1-12 carbons.

13. A compound according to claim 12 wherein $R_1$ and $R_2$ together represent a methylene group $-(CH_2)_n-$ where n is a whole number of from 1 to 6 and $R_3$ is a $-(CH_2)_4-$ group joining the 3- and 4-positions of the ring.

14. A compound according to claim 13 wherein $R_4$ is $-S(O)_pR_9$ where p is 0 and $R_9$ is a butyl group substituted with carboxy COOH.

15. A compound according to claim 14 wherein n is 3, p is 0, $R_9$ is $-CH_2C(CH_3)_2$ COOH and the $R_4$ is in the 4-position of the ring.

* * * * *